(12) United States Patent
Viator et al.

(10) Patent No.: US 7,322,972 B2
(45) Date of Patent: Jan. 29, 2008

(54) IN VIVO PORT WINE STAIN, BURN AND MELANIN DEPTH DETERMINATION USING A PHOTOACOUSTIC PROBE

(75) Inventors: John A. Viator, Portland, OR (US); Steven L. Jacques, Portland, OR (US); J. Stuart Nelson, Laguna Niguel, CA (US); Guenther Paltauf, Graz (AT)

(73) Assignee: The Regents of the University of California, Oakland, CA (US)

( * ) Notice: Subject to any disclaimer, the term of this patent is extended or adjusted under 35 U.S.C. 154(b) by 662 days.

(21) Appl. No.: 10/359,782

(22) Filed: Feb. 7, 2003

(65) Prior Publication Data

US 2004/0039379 A1  Feb. 26, 2004

Related U.S. Application Data

(60) Provisional application No. 60/371,900, filed on Apr. 10, 2002.

(51) Int. Cl.
*A61B 18/18* (2006.01)
(52) U.S. Cl. .......................................... 606/9
(58) Field of Classification Search ................ 600/595, 600/474, 300, 437, 463, 476, 473, 587, 407, 600/310, 306; 73/633
See application file for complete search history.

(56) References Cited

U.S. PATENT DOCUMENTS

| 5,348,002 | A | * | 9/1994 | Caro ........................... 600/310 |
| 5,701,902 | A | * | 12/1997 | Vari et al. .................... 600/473 |
| 5,792,049 | A | * | 8/1998 | Eppstein et al. ............. 600/306 |
| 5,840,023 | A | * | 11/1998 | Oraevsky et al. ............ 600/407 |
| 6,216,540 | B1 | * | 4/2001 | Nelson et al. ................ 73/633 |
| 6,381,488 | B1 | * | 4/2002 | Dickey et al. ............... 600/474 |

* cited by examiner

*Primary Examiner*—Max F. Hindenburg
*Assistant Examiner*—Fangemonique Smith
(74) *Attorney, Agent, or Firm*—Myers Dawes Andras & Sherman, LLP

(57) ABSTRACT

A photoacoustic probe for port wine stain (PWS), burn and melanin depth measurements is comprised of optical fibers for laser light delivery and a piezoelectric element for acoustic detection. The probe induced and measured photoacoustic waves in acryl amide tissue phantoms and PWS skin in vivo. Acoustic waves were denoised using spline wavelet transforms, then deconvolved with the impulse response of the probe to yield initial subsurface pressure distributions in phantoms and skin. The waves were then analyzed for epidermal melanin concentration, using a photoacoustic melanin index (PAMI) related to the amount of laser energy absorbed by melanin. Propagation time of the photoacoustic wave was used to determine the depth of blood perfusion underlying necrotic, burned tissue. Thus, the photoacoustic probe can be used for determining PWS, burn and melanin depth for most patients receiving laser therapy.

8 Claims, 31 Drawing Sheets

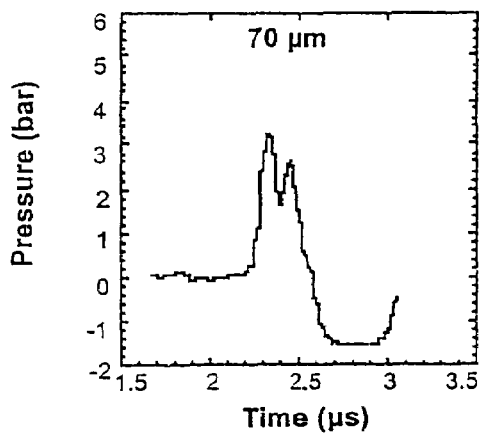
Fig. 5a
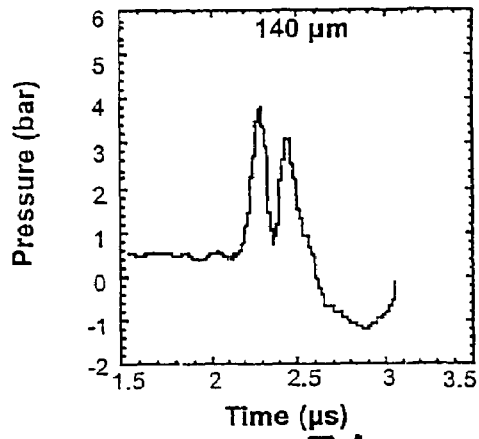
Fig. 5b
Fig. 5c
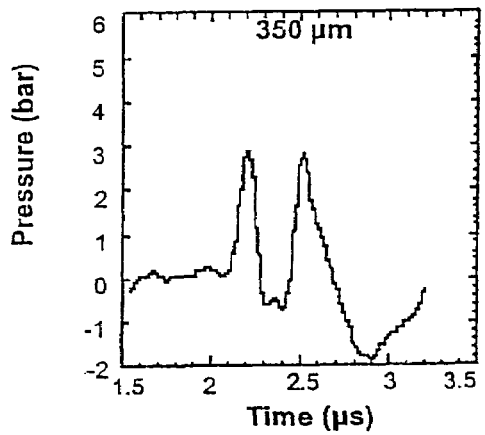
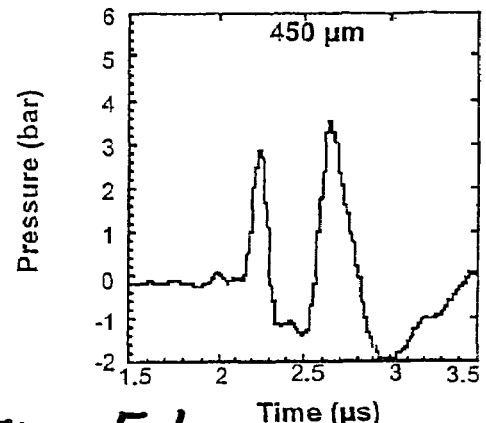
Fig. 5d
Fig. 5e
Fig. 5f
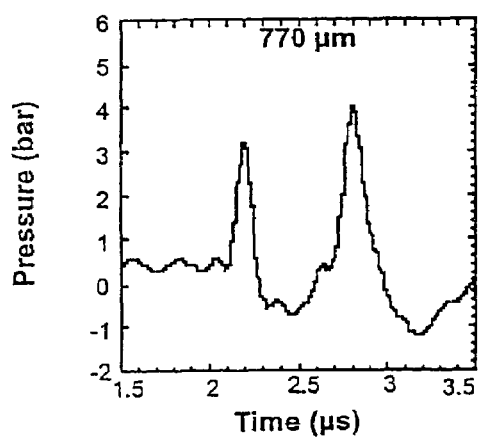
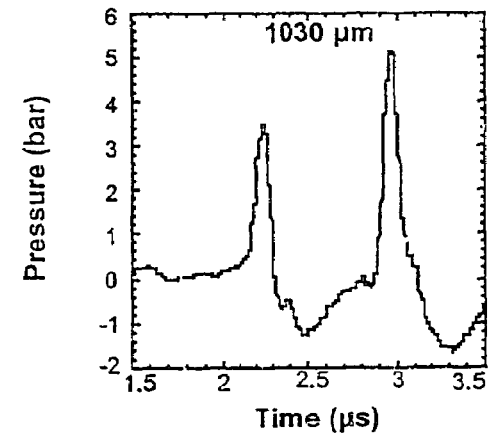

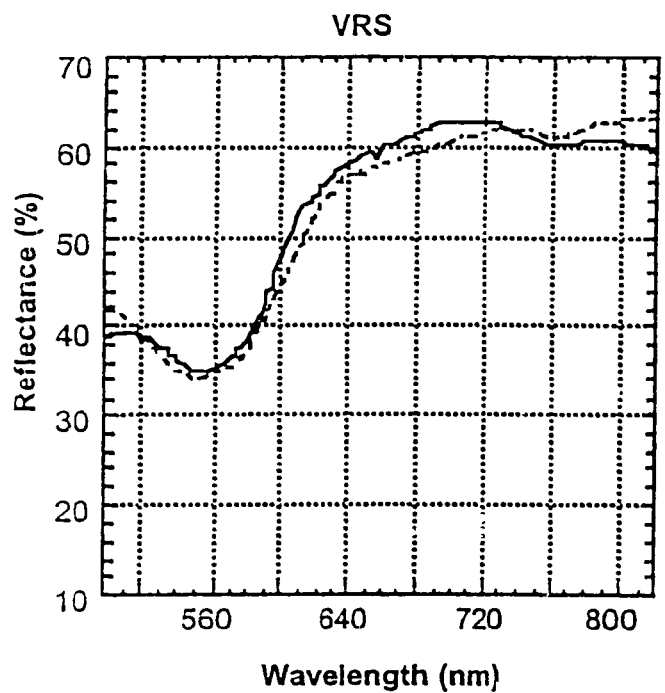
Fig. 27a
Fig. 27b
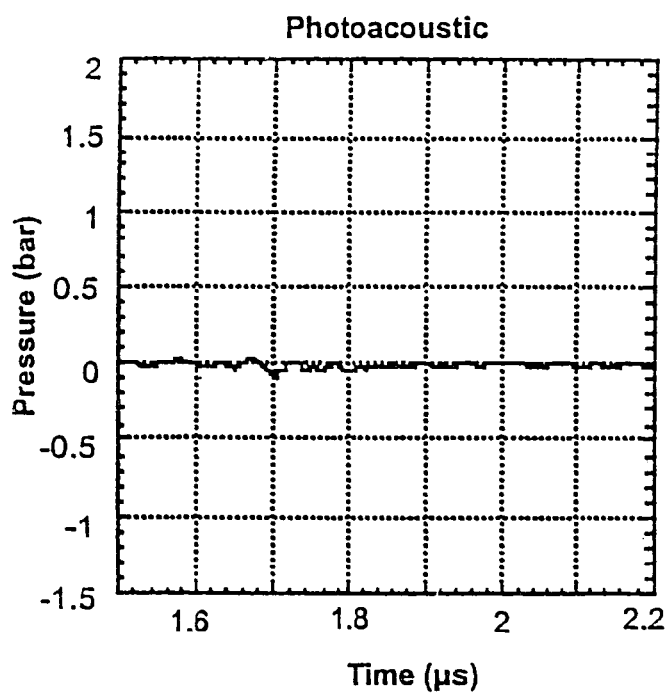

IN VIVO PORT WINE STAIN, BURN AND MELANIN DEPTH DETERMINATION USING A PHOTOACOUSTIC PROBE

RELATED APPLICATIONS

The present application is related to U.S. Provisional Patent Application Ser. No. 60/371,900, filed on Apr. 10, 2002, which is incorporated herein by reference and to which priority is claimed pursuant to 35 USC 119.

This invention was made with Government support under Grant Nos. AR43419 and GM62177, awarded by the National Institutes of Health. The Government has certain rights in this invention.

BACKGROUND OF THE INVENTION

1. Field of the Invention

The invention is related to the field of noninvasive depth profiling of skin parameters using a photoacoustic probe and in particular to depth profiling port wine stains, skin burns and melanin distributions or concentrations.

2. Description of the Prior Art

Laser treatment of port wine stain (PWS) lesions is an elective therapy for restoring normal appearance to human skin, though the success rate depends on many factors, including epidermal melanin concentration, lesion depth, and size of the blood vessels. Epidermal melanin, a broadband optical absorber, blocks laser energy and decreases fluence at the lesion. For human skin with a high concentration of melanin, skin types III or higher, epidermal temperature may rise to such levels that irreversible damage and scarring or dyspigmentation occurs.

As a preventive measure, clinicians have utilized skin cooling, such as cryogen spray cooling (CSC) to prevent epidermal damage while still treating the deeper PWS. Using CSC, a cryogen spray is directed onto the skin surface prior to and during laser irradiation and the epidermis cools nearly instantaneously. The PWS cools at some later time, preferably long after the therapeutic laser pulse has been delivered, causing irreversible thermal damage to the lesion.

Knowing the depth profile of the PWS skin, including the spatial relationship between epidermal melanin and blood vessels, the clinician may optimize CSC parameters for treatment on an individual patient basis. Thus, we have developed a photoacoustic probe for determining PWS depth quickly and noninvasively.

Burn trauma is a major cause of injury worldwide. Treatment of burns includes excision of irreversibly damaged tissue followed by skin grafting. Currently, the burn surgeon uses subjective, inexact methods for determining excision depth which may result in further damage to viable tissue. Burn trauma in the United States accounts for 3% of all injury deaths and approximately 50,000 acute hospitalizations per year. Treatment of burns includes wound excision and skin grafts. In order to optimize treatment, the burn surgeon must accurately determine the depth of thermal injury. Currently, burn depth estimates are based on appearance and sensory function, so accurate depth determination is subjective and inexact. An objective method to determine burn depth would not only provide the surgeon with a more accurate appraisal of damage, but may also allow field personnel to perform quick and accurate measurements that aid the treatment of burns.

Many methods proposed for burn depth determination simply attempt to ascertain if the injury will heal within 3 weeks, as wounds that spontaneously heal within that period usually do so without scarring or impairment. Wounds that take longer to heal require surgical intervention to prevent complications. Exact depth determination, however, would not only give an indication of the healing potential, but also aid the burn surgeon in the assessment of debridement depth, if warranted. If depth profiles of the wounds were available, the burn surgeon could accurately determine whether tissue is necrotic, reversibly damaged, or viable. Necrotic tissue must be debrided, while reversibly damaged tissue, overlying normal, viable tissue, must be allowed to heal. Debridement should occur quickly for more rapid wound closure, prevention of infection, and thus, shortened hospital stay.

The three tissue conditions noted above have contrasting optical properties, leading one to believe that an optical probing method might be useful for burn depth profiling. Unfortunately, optical signals degrade quickly in human skin owing to its highly scattering nature. Optical coherence tomography, spectroscopy, confocal imaging, fluorescence, and laser Doppler flowmetry are all dependent on preserving information contained in the optical signal, which degrades with each photon scattering event. Additionally, with the exception of polarization sensitive optically coherent tomography (PS-OCT), these methods do not give an absolute measure of burn depth, but seek to discriminate between superficial and deep burns.

The limitations of such optical methods must be considered in their implementation for diagnosis of burn injury. PS-OCT has been used to investigate burn depth. While burn depth was measured, as determined by loss of birefringence in collagen, PS-OCT is only capable of imaging the upper 1.5 mm of human skin. This depth would be insufficient to probe the entire dermis, which may be up to 5 mm deep.

While optical methods for probing burn depth will be hampered due to photon scattering by tissue, acoustic wave propagation in tissue is unaffected by such scattering. Moreover, since nearly all biological tissue has similar acoustic impedance, acoustic scattering in soft tissue is limited. Hence, an acoustic wave can travel through layered tissue with very little signal degradation. The success of conventional ultrasound relies on such a propagation environment. In fact, ultrasound has been used to study depth of burn injury. The efficacy of the ultrasound method relied on the ability to detect damage in the deep dermal capillary plexus. The result was not an exact measure of burn depth, but an estimate of whether the injury required surgical intervention or not.

Any dermatologic laser procedure must consider epidermal melanin concentration, as it is a broadband optical absorber which affects subsurface fluence, effectively limiting the amount of light reaching the dermis and targeted chromophores. An accurate method for quantifying epidermal melanin concentration would aid clinicians in determining proper light dosage for therapeutic laser procedures. While some researchers have been able to quantify epidermal melanin concentration non-invasively using visible reflectance spectroscopy (VRS), there is currently no way to determine the distribution of melanin in the epidermis.

Melanin, a broadband optical absorber, is found in the epidermis of human skin to varying degrees, determining skin color and affecting subsurface fluence of visible light after laser irradiation. Any dermatologic laser procedure using visible wavelengths must consider epidermal melanin concentration in the interpretation of diagnostic information or in dosage estimates for therapy. For example, laser therapy of port wine stain (PWS) must consider epidermal melanin concentration in order to optimize laser fluence and cryogen spray cooling parameters. Currently, epidermal melanin concentration can be estimated noninvasively by pulsed photothermal radiometry (PPTR), visible reflectance spectroscopy (VRS) and chromameter measurements. As PPTR requires analysis using inverse algorithms, determination of epidermal melanin concentration is extremely sensitive to input parameters which can give inconsistent results. VRS and chromameter measurements show repeatable measurements of epidermal melanin concentration, though they provide no depth information. Additionally, many VRS systems and chromameters utilize an integrating sphere which averages skin reflectance over a large area (e.g. >1 $cm^2$), making local estimates of melanin concentration impossible. Photoacoustics has been used to determine optical properties of tissue and to perform imaging. It has been demonstrated how to extract absorption and scattering from analysis of photoacoustic waves induced in tissue phantoms. The prior art has used photoacoustic analysis to detect embedded absorbers in phantoms and tissue.

What is needed is an objective, accurate means to measure burn depth.

BRIEF SUMMARY OF THE INVENTION

The invention is an apparatus for depth profiling subsurface skin structures comprising a handpiece for placement against the skin and at least one optic fiber for delivering a light pulse to the skin. An acoustic detector is disposed in the handpiece for receiving photoacoustic waves from the skin. A circuit is coupled to the acoustic detector for processing electrical signals generated by the acoustic detector. The invention can also be defined as including the source of light coupled to the optic fiber for generating the light pulse. In the preferred embodiment the source of light comprises a laser, but may include other types of light or energy pulses such as a flash lamp.

The handpiece defines a chamber which is liquid filled to enable acoustic coupling to the skin. The apparatus further comprises means for micropositioning the optic fiber with respect to the skin.

The optic fiber delivers a light pulse to the skin, causing instantaneous heating, thermal expansion and generation of a photoacoustic impulse. The acoustic detector is spaced apart from the skin to create an acoustic delay in response relative to the photoacoustic impulse to avoid introduction of noise unrelated to the skin response.

It is to be expressly understood that either one or a plurality of optic fibers may be deployed in which each optic fiber delivers a light pulse to the skin. The plurality of optic fibers each simultaneously deliver a light pulse to the skin at a single spot. The plurality of optic fibers deliver a light pulse to the skin at a plurality of wavelengths or at the same wavelength.

The acoustic detector comprises a piezoelectric acoustic pressure transducer.

The skin structure which is detected or profiled is a skin burn and the electrical signals generated by the acoustic detector are interpretable as depth profiles of the skin burn. In another embodiment the skin structure is a port wine stain and the electrical signals generated by the acoustic detector are interpretable as depth profiles of the port wine stain. In still another embodiment the skin structure is melanin and the electrical signals generated by the acoustic detector are interpretable as depth profiles of concentration of the melanin.

The invention is also defined as a method for depth profiling subsurface skin structures comprising the steps of generating a light pulse, delivering the light pulse to the skin, sensing acoustic waves generated in the skin in response to the delivered light pulse, and processing the sensed acoustic waves from the skin to derive measured data corresponding to the subsurface skin structures.

The step of generating a light pulse comprises generating a laser pulse with a pulse duration short enough such that the resulting acoustic energy consequently generated in the skin through thermoelastic expansion of the skin does not propagate outside of the volume of light absorption during the laser pulse.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIGS. 5a-5f are a series of graphs of the pressure verses time of the deconvoluted signal for port wine stain measurements showing separations of an epidermal peak and PWS peak. The bloodless dermis thickness is indicated at the top of each graph. Deeper PWS's correspond to greater separation of the two peaks.

FIGS. 27a and 27b are two graphs comparing VRS measurements on the left and photoacoustic measurements on the right of a subject with vitiligo. The small peak at 1.7 μs on the photoacoustic plot indicates minor absorption due to trace amounts of melanin in the epidermis.

Figure 1:
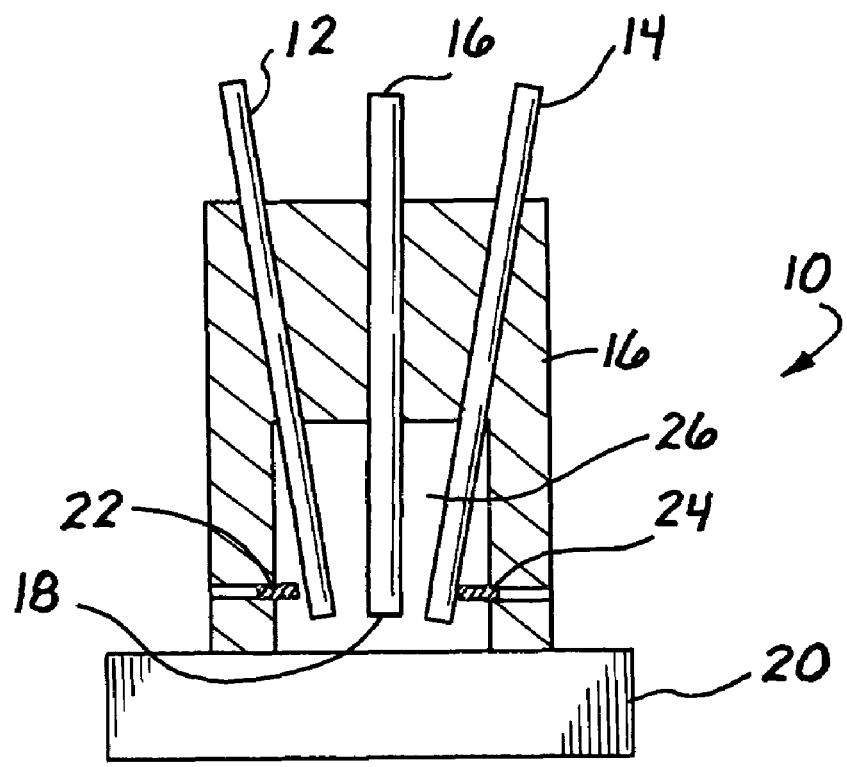
FIG. 1 is a side cross-sectional view of a simplified depiction of the handpiece of the invention used to deliver and sense the photoacoustic signals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

A photoacoustic method for determining burn depth might provide a means to exploit the ability to detect blood perfusion, as in the optical methods mentioned above, with the robustness of acoustic propagation through tissue, giving a real time, non-invasive determination of the exact depth of burn injury. Unlike the aforementioned optical methods, photoacoustic generation does not use photons as a signal, but as a means for delivering energy to subsurface blood vessels in the viable tissue underlying the thermally damaged layer. Once photon energy is absorbed, an acoustic wave is generated, which travels back to the skin surface where a detector measures acoustic wave shape and propagation time. Such data can be used to develop a depth map of the injured tissue.

We developed a photoacoustic probe 10 for non-invasive measurement of burn depth, consisting of an optical fiber delivery system coupled with a piezoelectric detector 18 for acoustic detection. A frequency doubled Nd:YAG laser 30 operating at 532 nm provided the laser energy for photoacoustic generation. Propagation time of the photoacoustic wave was used to determine the depth of blood perfusion underlying necrotic, burned tissue. We tested the probe on layered acryl amide phantoms with optical properties matched to those of human skin. We then tested the probe on burns of various depths induced on rats. We performed PS-OCT measurements to verify the photoacoustic analysis. Additionally, we took biopsies from the animals and conducted histological analysis to determine the extent of thermal damage in the tissue. Burn depths determined by histology, PS-OCT, and photoacoustic means were compared and reconciled to within the limitations of interpreting the different methodologies.

For depth profiling of melanin concentration, the photoacoustic probe of the invention generated acoustic pulses in epidermal melanin. Laser light was delivered via an optical fiber integrated into the probe, which contained a piezoelectric element that detected photoacoustic waves. The waves were then analyzed for epidermal melanin concentration, using a photoacoustic melanin index (PAMI) related to the amount of laser energy absorbed by melanin. We compared the PAMI with the melanin concentration determined using VRS. Spectra from human skin was fitted to a model based on diffusion theory which included parameters for epidermal thickness, melanin concentration, hair color and density, and dermal blood content. We tested 20 human subjects with skin types I-VI using the photoacoustic probe and reflectance methods. A plot of PAMI v. VRS showed a good linear fit with $r^2=0.85$. We also present photoacoustic and VRS data for a human subject with vitiligo.

The photoacoustic probe of the invention is capable of determining the epidermal melanin concentration in human skin. Laser energy is delivered via the optic fiber to the skin surface, where it is absorbed by epidermal melanin. The short pulse duration of the laser ensures transduction of optical energy into acoustic waves, analysis of which gives the exact distribution of absorbed energy which, in turn, is related to the spatial distribution of melanin from which its concentration can be deduced. Thus, acoustic wave analysis provides the initial absorbed energy distribution of a therapeutic laser pulse, giving the clinician valuable information regarding light dosage.

Consider the apparatus for PWS profiling. A photoacoustic probe 10 for port wine stain (PWS) or burn depth measurements is comprised of optical fibers 12, 14 for laser light delivery and a piezoelectric detector 18 for acoustic detection. The probe 10 induced and measured photoacoustic waves in acryl amide tissue phantoms, and PWS and burns in skin in vivo. The optical properties of the phantoms were chosen to mimic those of PWS and burned skin. Acoustic waves were de-noised using spline wavelet transforms, then deconvolved with the impulse response of the probe 10 to yield initial subsurface pressure distributions in phantoms, PWS and burned skin.

In the case of PWS using the phantoms, we determined the limit in resolving epidermal and PWS layers was less 70 µm. Additionally, we used the phantoms to determine that the maximum epidermal melanin concentration that allowed detection of PWS was between 13 and 20%. In vivo measurements of PWS skin with different epidermal melanin concentrations correlated with the phantoms. Thus, the photoacoustic probe is proven for use in determining PWS depth for most patients receiving laser therapy.

Burn depth measurements were made using a photoacoustic probe 10 which delivered to the burn site via a 1000 µm diameter optical fiber 34, 4 ns pulses of 532 nm laser light from a Q-switched Nd:YAG laser 30. Acoustic pulses were generated by absorption of laser light in viable blood vessels beneath the necrotic, burned layer. The acoustic signals were detected by a piezoelectric detector 18 within the probe 10 and the acoustic propagation time was used to determine burn depth. The probe 10 was tested on 200-500 µm thick polyacrylamide tissue phantoms with optical properties matched to those of burned and viable skin. The photoacoustically determined depths of the phantoms were approximately 50 µm greater than actual depths.

The probe 10 was then tested on an in vivo rat model burned with a brass rod heated to 75 C for 5, 10, 20, or 30 s. The photoacoustically determined burn depths were within 20 µm of depth measurements obtained using polarization sensitive optical coherence tomography (PS-OCT). Histological samples and microscopically examined structures were compared to the photoacoustic data.

Photoacoustic depth profiling of the invention uses pulsed laser irradiation to induce rapid thermoelastic expansion in targeted chromophores. This process is distinct from photoacoustic methods using modulated continuous wave irradiation, such as photoacoustic spectroscopy. Photoacoustic generation by thermoelastic expansion can be conceptually described as laser energy being quickly absorbed by a small volume such that resultant heating induces rapid expansion that manifests itself as a transient pulse of acoustic energy. Thermoelastic expansion occurs when the condition of stress confinement is achieved i.e., where optical energy is deposited before the energy can propagate away acoustically. This condition is expressed as $t_p < \delta/c_s$, here $t_p$ is the laser pulse duration, $\delta$ is the absorption depth of laser energy, and $c_s$ is the speed of sound in the medium. If the radiant exposure is not excessive, the resulting acoustic waves behave according to the linear wave equation. Furthermore, if the laser spot diameter is much larger than $\delta$, then a simple plane wave analysis can be used, allowing acoustic propagation time to be used as an indicator of distance traveled. If stress confinement, linearity, and plane wave geometry are preserved, depth profiling and imaging of layered tissue may be achieved by simple photoacoustic analysis.

The use of photoacoustic techniques is ideally suited for the application of determining skin structure due to the robustness and high resolution of the acoustic signal. Hence, analysis of photoacoustic waves has been used to investigate layered structures in biological tissue. The prior art has derived optical properties of absorbing solutions by fitting the photoacoustic signal to Beer's law. One of the inventors of the present application has derived an iterative scheme for determining the absorption coefficient of layered gels and stained elastin from photoacoustic waves, and has developed an endoscopic photoacoustic probe for determination of treatment depth after photodynamic therapy for esophageal cancer. This same inventor has developed a probe to determine the epidermal and PWS blood vessel depths in human subjects using a photoacoustic reflectance probe. We present an evaluation of this photoacoustic probe used for PWS depth to determine the limitations of its use in human patients.

The photoacoustic probe is comprised of a small, acrylic handpiece which combines two optical fibers and a piezoelectric element, used to map the depth distribution of epidermal melanin and PWS. We present measurements with tissue phantoms that show the minimum separation with which these two layers can be discriminated. We also use phantoms to show the maximum epidermal melanin content that allows threshold detection of the PWS layer. The raw photoacoustic signals from phantoms and human subjects were denoised using wavelet transforms and deconvolved with the probe's impulse response to give the approximate initial pressure distribution after the laser pulse.

The probe 10 is shown schematically in FIG. 1. It is comprised of two 1500 µm diameter optical fibers 12 and 14 terminating into a cylindrical acrylic cylindrical handpiece 16, which in the illustrated embodiment is 22 mm long and 16 mm in diameter. An acoustic transducer detector 18 within the probe 10 sent a signal via a 10 Ω coaxial cable 16 to an oscilloscope (not shown, Tektronix TDS 3014, Wilsonville, Oreg.) with a bandwidth of 100 MHz. The input impedance of the oscilloscope was 1M Ω. The laser spots from optical fiber 12 and 14 were slightly elliptical with a diameter of approximately 2 mm. The radiant exposure at the surface of the target or skin 20 was 0.70 J/cm$^2$. The optical fibers 12 and 14 were steered via set screws 22 and 24 respectively within the acrylic handpiece 16 so that both laser spots from fibers 12 and 14 were coincident. The probe 10 was placed in contact with the target 20 so that the photoacoustic waves were generated directly below the acoustic detector 18. A 1.1 mm diameter semi-rigid coaxial cable 16 (UT-43-10, Micro-Coax, Pottstown, Pa.) was inserted into the probe 10 with a piezoelectric film or detector 18 (polyvinylidene fluoride (PVDF), K-Tech, Albuquerque, N. Mex.) attached to the end. The active area of the acoustic detector 18 was 700 μm in diameter. Thus, the optical fibers 12 and 14 irradiated the tissue surface of target 20, inducing photoacoustic waves, which were sensed in reflection mode by the PVDF detector 18. The fibers 12, 14 and detector 18 were housed in a water filled chamber 26 defined in handpiece 16, which allowed for acoustic impedance matching between the surface of target 20 and detector 18. The acoustic detector 18 was recessed approximately 3 mm into the probe housing 16 to separate the target surface from the detector 18. This separation created an acoustic delay line of about 2 μs which prevented electrical noise, caused by the laser pulse and occurring at 0-0.5 μs, from contaminating the photoacoustic signal which was transmitted via the coaxial cable 16 to an oscilloscope 28 shown in FIG. 2.

Figure 2:
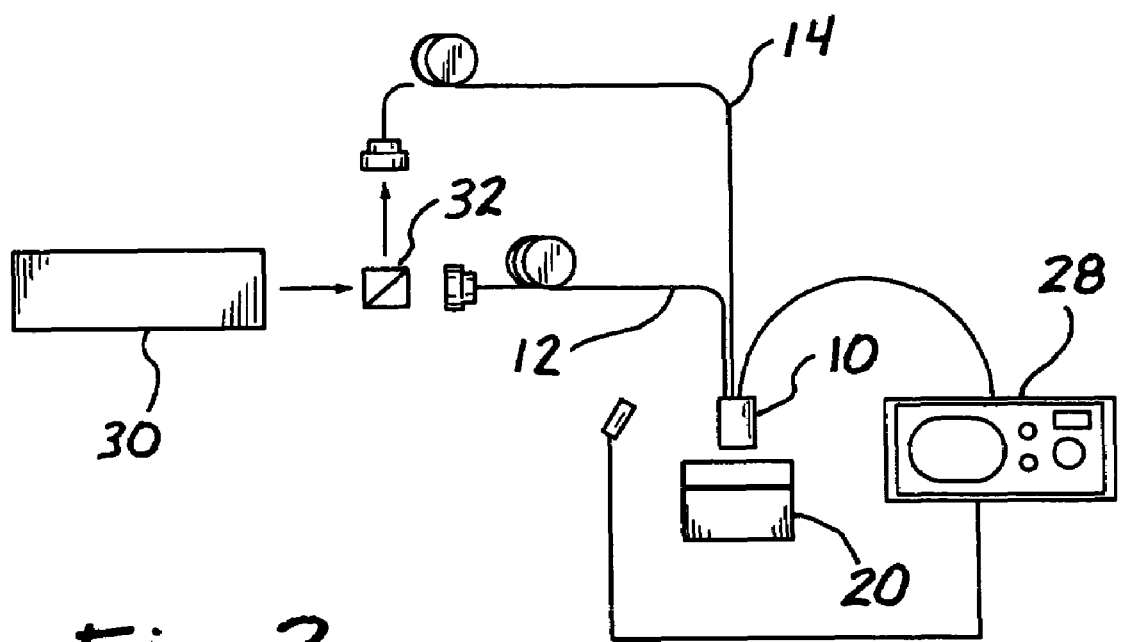
FIG. 2 is a schematic diagram of the system in which the handpiece of FIG. 1 is used.

The experimental apparatus is shown in FIG. 2 and is comprised of a frequency-doubled, Nd:YAG laser 30 operating at 532 nm with a 4 (FWHM) pulse duration. Laser light was coupled into two optical fibers 12 and 14 via a cube beamsplitter 32. Two fibers 12 and 14 were used to increase the total amount of energy delivered, though energy was limited to less than 22 mJ to keep patient discomfort to a minimum. Subsequent photoacoustic analysis was done on a Macintosh computer (G4 Powerbook, Apple Computer, Cupertino, Calif.).

The detector 18 was calibrated by conventional means by inducing photoacoustic waves in solutions where the absorption coefficient was known. The PVDF detector 18 detected the waves in a transmission setup. The free beam of the laser 30 was used, providing a large spot, which minimized diffraction and delivered more energy. The detector 18 was immersed in an absorbing solution and centered directly above the laser spot. The laser spot diameter was 4.6 mm. The radiant exposure was 0.084 J/cm$^2$ as calculated by measuring total energy with a standardized photodetector, (Molectron, Beaverton, Oreg.) and dividing by the spot size. The absorption coefficients of the solutions were 51, 103, 148, 197, and 239 cm$^{-1}$ at 532 nm. The equation $$p(0) = \tfrac{1}{2}\Gamma H_0 \mu_a \quad (1)$$

was used to predict the photoacoustic pressure (J/cm$^3$). $\Gamma$ is the Grueneisen coefficient, which models the fraction of optical energy converted to acoustic energy. In this analysis, $\Gamma = 0.12$ was used. $H_0$ is the radiant exposure (J/cm$^2$), and $\mu_a$ is the absorption coefficient of the solution in cm$^{-1}$. Finally, the conversion 10 bar=1 J/cm$^3$, was used to determine a calibration factor of mV/bar for the acoustic detector by dividing the amplitude of the acoustic waveform by the calculated pressure. The calibration factor was 1.31 mV/bar.

Tissue phantoms were made with 20% acryl amide in water with added dye for absorption and fat emulsion for scattering. The amount of dye and fat emulsion were chosen to mimic optical properties of human skin. Direct Red 81 (Sigma Chemical, St. Louis, Mo.) was used to simulate hemoglobin absorption and Intralipid (Abbott Laboratories, North Chicago, Ill.) to induce light scattering. A 1% Intralipid solution was used to approximate 200 cm$^{-1}$, the approximate scattering coefficient of human skin at 532 nm. The two types of phantoms prepared were comprised of three layers, representing epidermis, bloodless dermis, and PWS. Acryl amide solutions were injected between glass slides with plastic feeler gauge stock of various thicknesses used as spacers (Feeler gauge stock, McMaster-Carr, Los Angeles, Calif.).

In the first set of experiments, the minimum distance that the probe could discriminate between the two absorbing layers (epidermis and PWS) was studied. These epidermal and PWS layers were entirely absorbing with absorption coefficients of 25 cm$^{-1}$, and the bloodless dermis layer was clear. In the second set of experiments, phantoms were turbid. These experiments were meant to determine the maximum epidermal melanin concentration that would allow detection of a photoacoustic signal from the PWS. Each layer experiment was performed once on each phantom, though the reported measurements were averages over 64 laser pulses.

The epidermal layers were 100 μm thick and the PWS layers approximately 1 mm thick. The bloodless dermis layers were 70, 140, 350, 450, 770, and 1030 μm thick. The three layers were placed on top of each other. Enough moisture was present to ensure acoustic coupling and any air pockets were removed. After laser irradiation, layers were measured with a micrometer (Digital Micrometer, Mitutoyo, Aurora, Ill.) with an accuracy of approximately 20 μm. The epidermal thickness was subtracted from photoacoustically derived thicknesses to deduce the thicknesses of the bloodless dermis layers. Photoacoustic peak-to-peak times were derived from the epidermal surface to the PWS layer, thus the depths indicated by the peak to peak time included the epidermal thickness and needed to be subtracted.

To model skin with various epidermal melanin concentrations, turbid phantom layers were used with a scattering coefficient of approximately 200 cm$^{-1}$. The optical absorption was varied to model 2, 5, 13, and 20% epidermal melanin volume fractions, corresponding to typical values for skin types I, II, III, and IV. We assumed a melanin absorption coefficient of 400 cm$^{-1}$ at 532 nm. The optical depths corresponded to 0.06, 0.15, 0.39, and 0.60, as layer thickness was 75 μm. Optical properties and layer thicknesses of the phantoms are shown in Table 1.

TABLE 1

(Optical properties and layer thicknesses of phantoms used for the experiments for determining the maximum epidermal melanin concentration for threshold detection of a photoacoustic PWS signal.)

| Layer | Thickness (μm) | $\mu_a$ (cm$^{-1}$) | $\mu_s$ (cm$^{-1}$) | Optical depth |
|---|---|---|---|---|
| epidermis | 75 | 8, 20, 52, 80 | 200 | 0.06, 0.15, 0.39, 0.6 |
| dermis | 250 | 0.2 | 200 | 0.005 |
| PWS | 1000 | 25 | 200 | 2.5 |

We also tested three healthy human subjects using the photoacoustic probe 10. The subjects had skin phototype I-II, III, and IV. PWS birthmarks were on the face and arms. All subjects indicated little or no sensation during laser irradiation. Individual tests took approximately 10 minutes and preceded normal laser therapy for PWS. The raw signal from the photoacoustic probe 10 was a convolution of its impulse response and actual pressure induced by the laser pulse. This assertion is reasonable in that photoacoustic generation and propagation are described by the linear wave equation and hence the probe constitutes a linear, time invariant system. Analysis of waveforms from phantoms of known dimensions showed a broadening, or smearing, from what would be expected from the pressure signals. This smearing was also evident in the raw signals from human subjects, as the breadth of the epidermal signal exceeded the normal range of skin thicknesses. Smearing was due to the relatively large photoacoustic source, due to the large laser spot, compared to the small active area of the acoustic detector 18. Such an extended source is detected by the small detector 18 as a single signal over a time period related to the dimensions of the source (laser spot diameter). After determining the probe impulse response, we performed a simple deconvolution on all signals to produce the initial pressure distribution of each experiment.

Prior to deconvolution, we denoised the photoacoustic signals to obtain optimal deconvolution using our algorithm. Denoising was achieved by two means: signal averaging during the experiment and post-experiment using wavelet shrinkage techniques. During the experiment, the signals were averaged over 64 laser pulses to minimize random noise. Longer averages were not taken due to dynamic processes that could change the photoacoustic signal, such as subject movement. Further denoising was accomplished with wavelet transforms, using Wavelet Explorer (Wolfram Research, Inc., Urbana, Ill.), an add-on of Mathematica.

Figure 3:
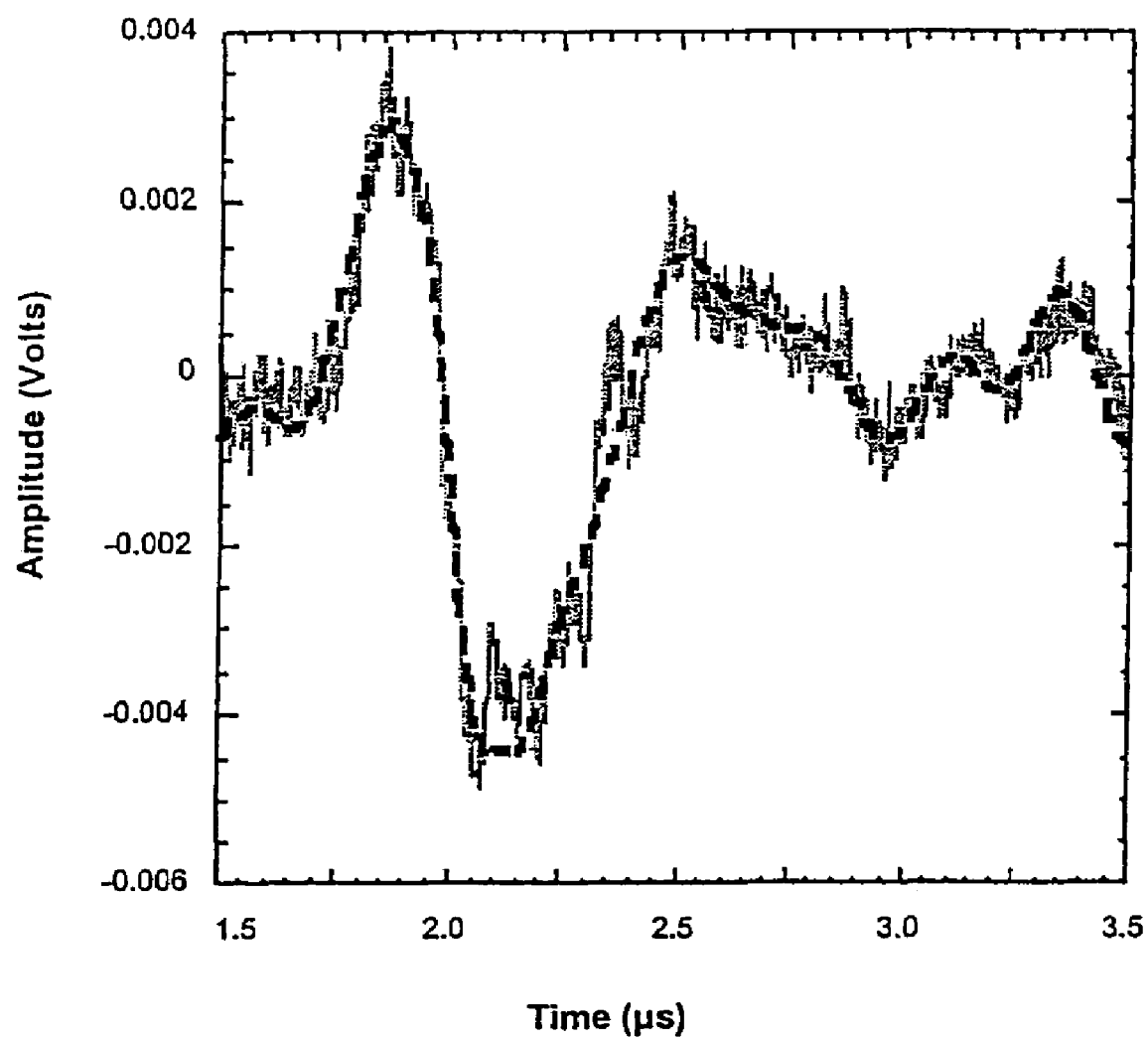
FIG. 3 is a graph of the photoacoustic signal of the handpiece of FIG. 1 verses time shown in dotted outline in a denoised version derived using wavelet soft thresholding.

Spline wavelets were chosen as the expected pressure signal was suited to relatively low order polynomial fits, verified by visual inspection of the noisy signals. The denoising algorithm used 4-level spline wavelet transforms and the threshold level was obtained by estimating the noise level on each signal. Threshold was selected by taking a value between the noise level and the smallest signal variation, with the threshold set closer to the noise level. An example of wavelet denoising of a photoacoustic signal is shown in FIG. 3.

The initial pressure distribution generated by absorption of laser light was determined by deconvolving the photoacoustic signal with the probe impulse response which was determined by irradiating a highly absorbing acryl amide gel with the probe 10. Ideally, an impulse response would require a target of infinite absorption, but practically, an absorption coefficient higher than the ability of the system's resolution would be sufficient. Probe resolution is limited by the laser pulse duration, $T_p$. Using the speed of sound in tissue, $c_s$, approximately 1.5 mm/μs, the resolution limit due to laser pulse duration is $\epsilon_p = c_s T_p = 6$ μm. An absorption depth of 6 μm corresponds to an absorption coefficient ($\mu_a$) of about 1700 cm$^{-1}$. We used an acryl amide phantom of 1 mm thickness with a $\mu_a$ of 1500 cm$^{-1}$ as making a phantom of higher absorption was not possible using Direct Red. Radiant exposure for determining the impulse response was approximately 0.5 mJ/cm$^2$.

Figure 4:
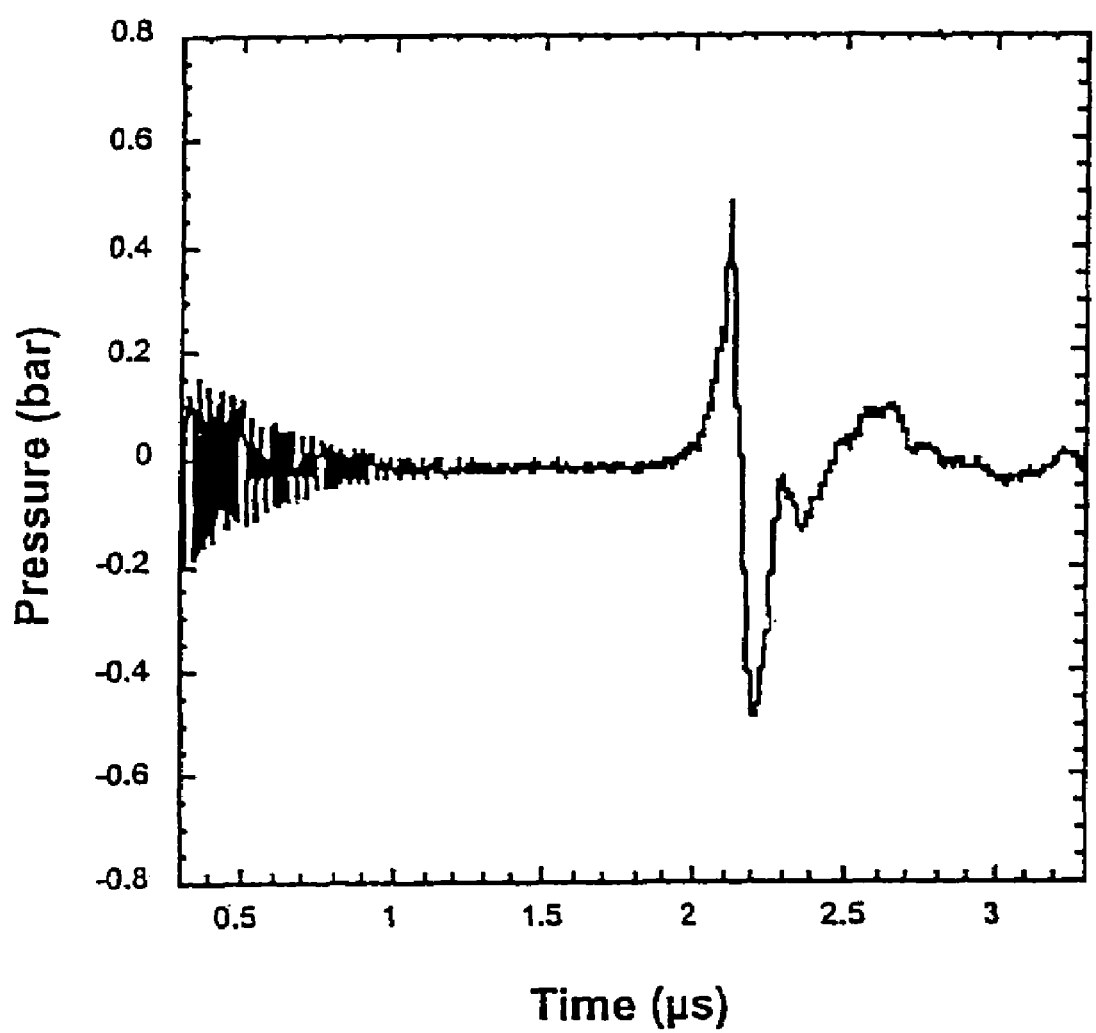
FIG. 4 is a graph of the impulse response of the handpiece of FIG. 1 verses time obtained by irradiating an acryl amide phantom.
Figure 6A:
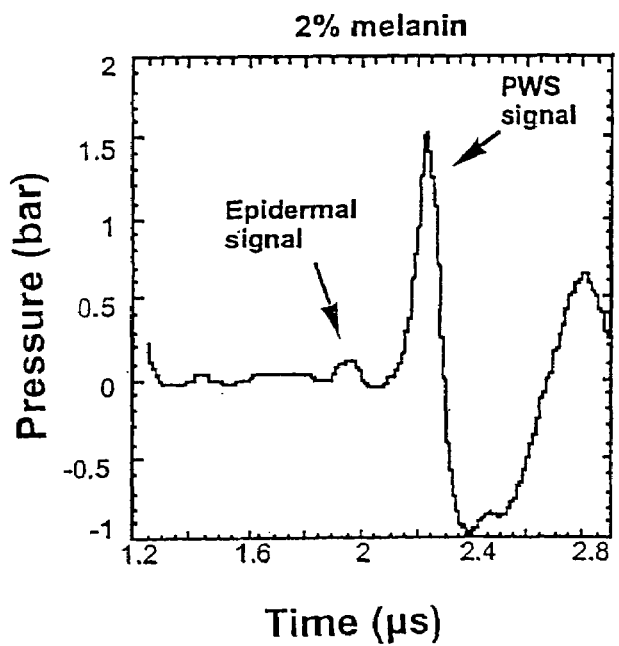
FIGS. 6a-6d are a series of graphs of the pressure verses time of the deconvoluted signal for epidermal melanin layers modeled by absorbing superficial layers in tissue phantoms showing PWS signals for 2, 5, 13% melanin concentrations, but none for 20% melanin concentration.
Figure 6B:
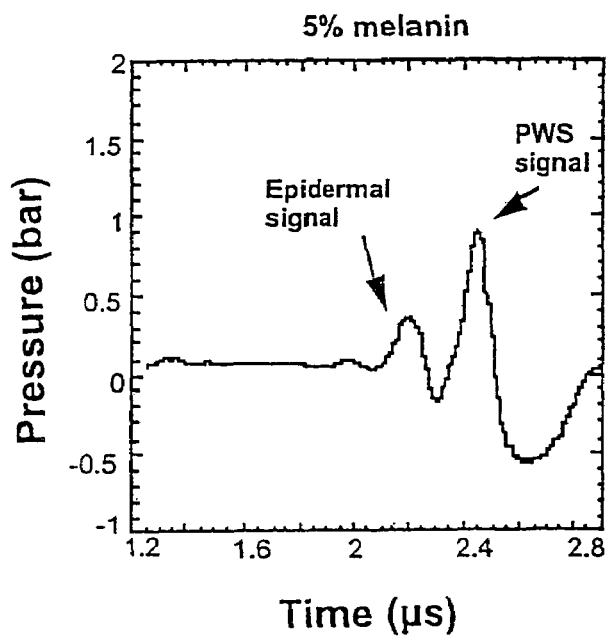
Figure 6C:
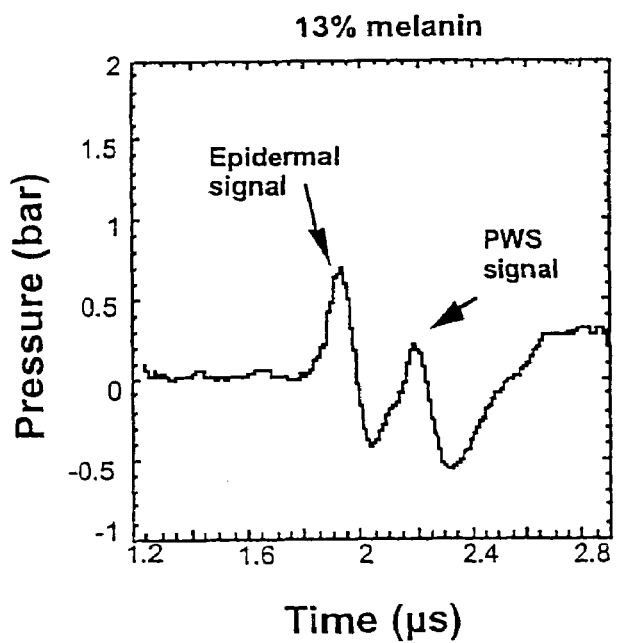
Figure 6D:
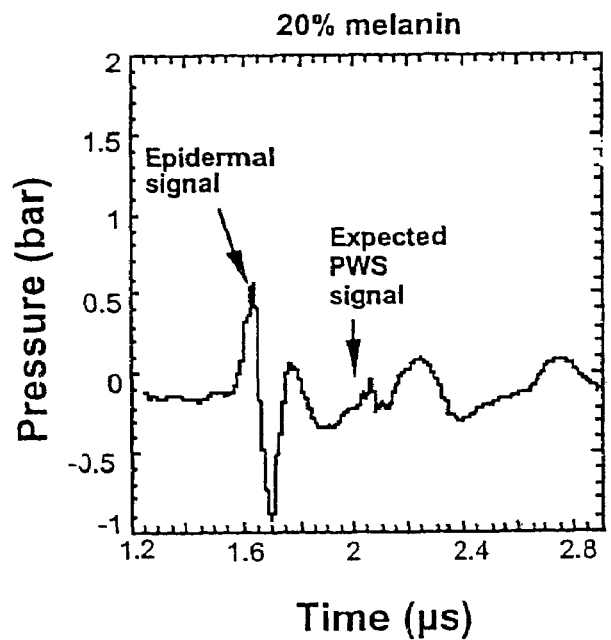
Figure 7A:
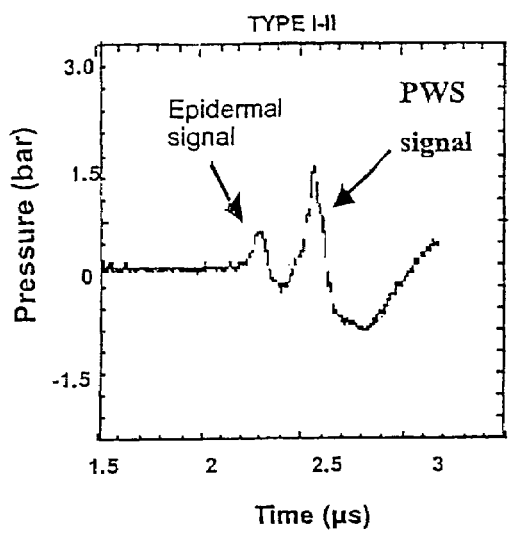
FIG. 7 is a series of graphs of the pressure verses time of the deconvoluted signal for four PWS patients having different skin types.
Figure 7B:
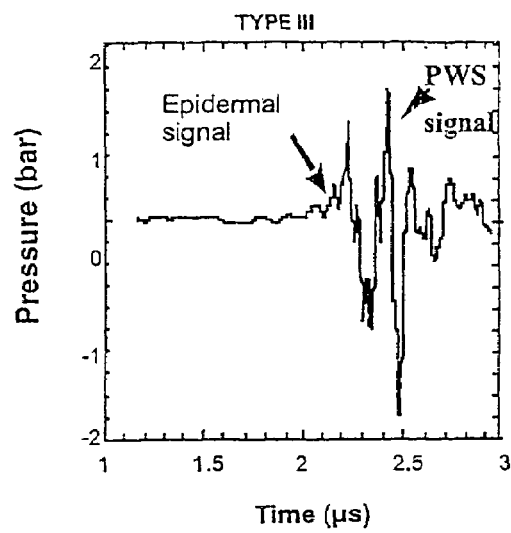
Figure 7C:
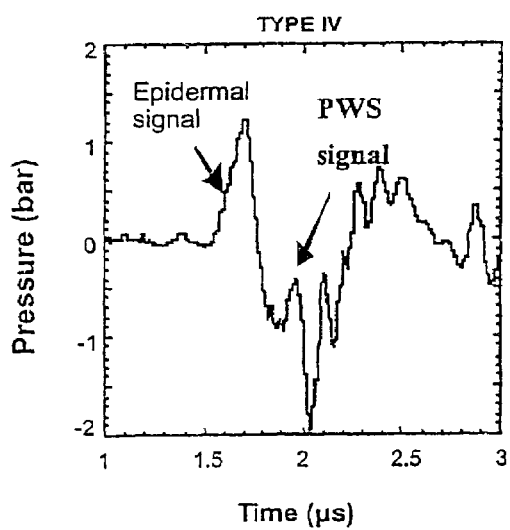
Figure 7D:
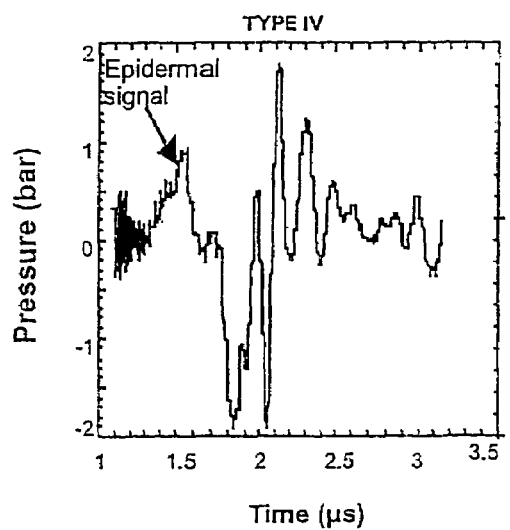

The resulting impulse response is shown in FIG. 4. Diffraction is evident beginning at 2.3 μs, though this region was not included in the deconvolution algorithm. Once the impulse response was determined, photoacoustic signals were deconvolved by taking the Fourier transforms (FFT) of the impulse response and signal, $$H(\omega) = FFT(h(t)) \quad (2)$$

$$P(\omega) = FFT(p(t)) \quad (3)$$

where h(t) is the impulse response and p(t) is the photoacoustic signal. Deconvolution was performed by a smooth division by zero routine, $$S(\omega) = P(\omega)H(\omega)/(H(\omega)^2 + \delta^2) \quad (4)$$

where $S(\omega)$ is the FFT of the true pressure signal and δ is an arbitrarily small quantity. For these experiments, $\delta \cdot 10^{-4}$ of the transform values. This scheme was used to prevent division by zero from regions of the impulse response's spectrum with no frequency information. The result of this division scheme at such points would result in $S(\omega) = 0$. The deconvolution scheme was implemented in Mathematica.

A series of photoacoustic waves is shown in FIGS. 5a-5d representing laser irradiations of three layered phantoms with clear layer separations of 70, 140, 350, 450, 770, and 1030 μm each. The separation of acoustic peaks corresponds to bloodless dermis layer thickness. The thicknesses of the phantoms, as determined by the micrometer measurements, are compared to the photoacoustically determined thicknesses in Table 2.

TABLE 2

Actual thicknesses of layered acrylamide phantoms v. thicknesses determined photoacoustically.

| Phantom | Actual Thickness (μm) | Photoacoustic Thickness (μm) | % Difference |
|---------|----------------------|------------------------------|--------------|
| 1 | 70 | 80 | 12% |
| 2 | 140 | 133 | −5% |
| 3 | 350 | 350 | 0% |
| 4 | 450 | 500 | 10% |
| 5 | 770 | 790 | 3% |
| 6 | 1030 | 980 | −5% |

A series of the photoacoustic waves from the epidermal filtering experiments is shown in FIGS. 6a-6d. The second peak, representing the PWS layer, is evident in the samples with 2, 5, and 13% melanin concentrations. The PWS layer is obscured in the sample with 20% melanin concentration.

In vivo photoacoustic measurements of PWS in human skin are shown in FIGS. 7a-7d. Skin types I-II, III, and IV are shown.

The photoacoustic probe 10 described above is well suited for determining PWS depth and its relation to the overlying epidermal melanin layer. Photoacoustic propagation is robust in tissue, showing little attenuation and scattering in the depths of a PWS lesion. However, the limits of the probe 10 to investigate PWS depth are dependent on epidermal melanin concentration. Thus, we performed experiments on tissue phantoms to determine these limits.

Tissue phantoms were used so that the accuracy of depths of absorbing layers could be determined. The typical discrepancy between the actual depth measured by micrometer and the photoacoustic probe was about 5%. The greatest discrepancy was less than 13%. The minimum depth discrimination between layers was 70 μm, as acryl amide layers could not be made any thinner. The actual ability of the probe to discriminate absorbing layers may be 50 μm or less, as 70 μm phantoms had photoacoustic peaks clearly distinguishable from each other. The theoretical limit of depth discrimination is dependent on the laser pulse duration. With a pulse duration of 4 ns, the resolution limit is 6 μm, as the speed of sound in tissue is approximately 1.5 mm/μs.

In practice, discriminating layers also involves signal duration, which depends on absorption depth of a layer and the actual layer thickness. Extrapolating from the phantom experiments, such a limit is approximately 50 μm. Although the phantom experiments showed promising results for depth profiling, it is important to consider the differences between an idealized phantom, in which anatomical structures are represented by planar layers, and the in vivo case.

PWS lesions are composed of many individual blood vessels within the dermis and only approximate a planar layer in shape. Additionally, the epidermal-dermal junction is not necessarily planar, but may have numerous papillae the dimensions of which are comparable to the epidermal thickness. These non-planar structures would contribute to the differences between the phantom measurements and in vivo measurements, where diffraction may make substantial contributions to the photoacoustic signal. A comparison of the waveforms in FIG. 6 and FIG. 7 illustrates this difference, where the in vivo measurements show considerable diffraction, particularly in the latter part of the signal.

Figure 8A:
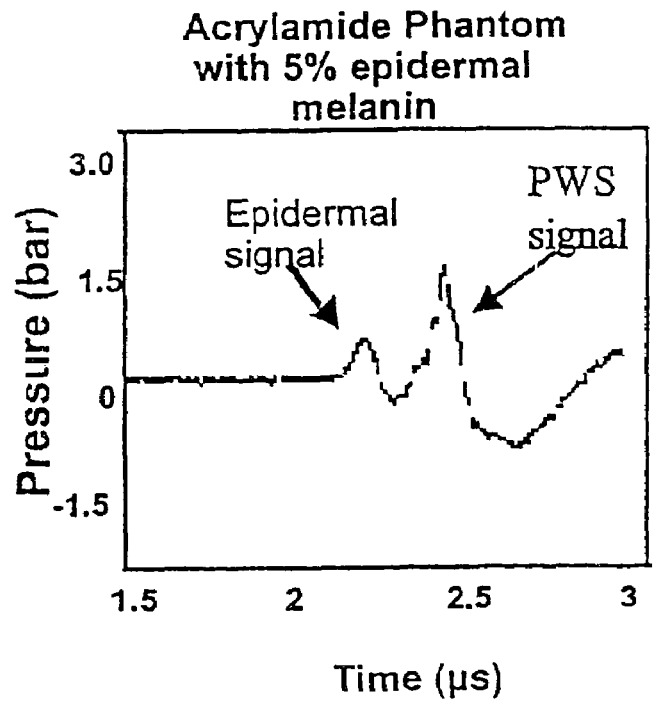
FIGS. 8a-8b are two graphs of the pressure verses time of the deconvoluted signal for an acryl amide phantom with 5% epidermal melanin shown on the left and a PWS patient with skin Type I-II.
Figure 8B:
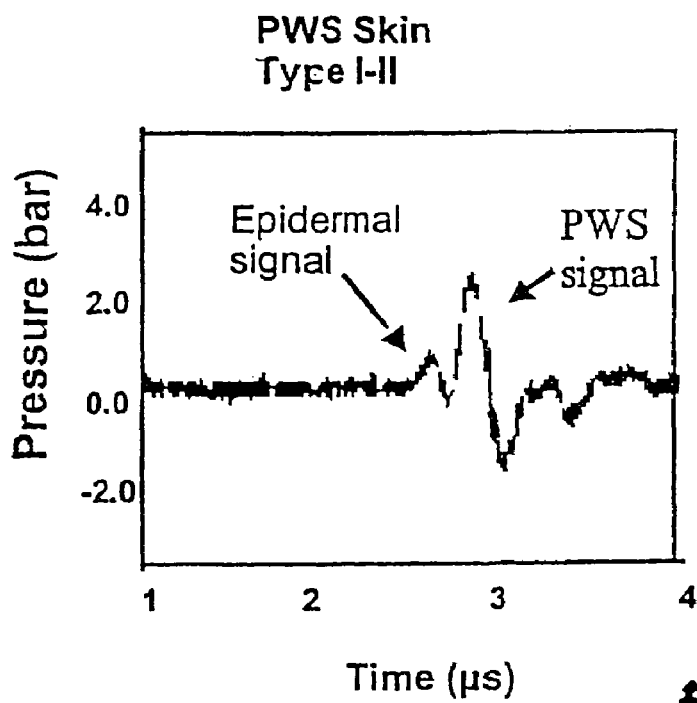

Phantoms were constructed with optical properties closely mimicking human skin. The photoacoustic signal from a three layer phantom is shown in FIG. 8a next to a signal from in vivo human PWS skin in FIG. 8b. The phantom was made to simulate 5% melanin volume fraction, corresponding to skin type II. The signal from the PWS skin was taken from a human subject with skin type I-II.

Though the actual pressures are different between the phantom and PWS skin, the two signals are similar. The pressures are different because the signals were taken at different times and the probe 10 was not necessarily optimized during the phantom measurement. Nevertheless, the similarity justifies the use of turbid acryl amide phantoms for simulating PWS skin.

Results of the epidermal melanin filtering in FIG. 6 showed that the probe could detect the PWS signal for skin with melanin volume fraction of up to 13%. However, the PWS signal was obscured by a phantom simulating a melanin volume fraction of 20%. The second photoacoustic peak in the 20% signal was not the PWS layer, as the distance between layers indicated by the time separation of the two peaks was approximately 130 µm, or about half the true separation. The second peak was merely the PWS signal being obscured by diffraction from the epidermal melanin layer.

In vivo measurements were taken from three PWS patients with skin type I-II, III, and IV. The same probe 10 was used for the current in vivo measurements. Actual depth relationships between epidermal melanin layers and PWS lesions were not determined by biopsy, but the acoustic waveforms were consistent with turbid phantom experiments. The temporal delays in the photoacoustic signals from the epidermal melanin and PWS layers corresponded with the phantoms, as well as their relative amplitudes. Ideally, photoacoustic signals, after denoising and deconvolution, should be an accurate representation of PWS anatomy, in vivo.

The signal processing in these experiments was performed to reconstruct the initial pressure distributions in tissue and phantoms immediately after laser irradiation. Raw data from the photoacoustic probe clearly did not represent the initial pressure as signals from the layered phantoms indicated layer thicknesses that were greater than the actual phantom materials. Additionally, raw signals from in vivo PWS skin showed epidermal melanin layers thicker than the known thickness of the entire epidermis. We performed deconvolution of the raw data with the instrument response function, resulting in a better approximation of the actual pressure distribution, though the deconvolution scheme did not give an entirely accurate reconstruction. We improved the deconvolution scheme by increasing the signal to noise ratio using wavelet denoising, though reconstructions were still not perfect. Reconstruction of absorbing tissue phantoms still showed broader signals than expected, though better than the raw signals themselves. Wavelet thresholding successfully denoised the signals, while still preserving salient features. Threshold was chosen after visual inspection of the signal and estimation of the noise level. Denoising was performed using different threshold levels, above and below the estimated noise level. Most thresholds were set at approximately 2-3 times the noise level.

In conclusion, the photoacoustic probe 10 above is suited for depth measurements of PWS subjects with skin types I-III and some subjects with skin type IV, as it has the ability to resolve lesions from epidermal melanin to within 70 µm. The probe 10 is non-invasive and causes no patient discomfort, due to the low laser fluence. Robust signals from tissue phantoms at 325 µm depth indicate that the probe 10 could be used for most PWS patients, given the limitation of epidermal melanin content. Laser treatment of PWS patients with skin type IV or greater is difficult, so the current probe 10 can perform PWS depth determination for most patients receiving laser therapy. The probe 10 successfully detected PWS lesions in patients with skin types I-IV, giving a suggested depth relationship between the epidermal melanin layer and PWS. Finally, better reconstruction algorithms may be implemented to improve upon the probe's ability to determine the actual depth profiles of subsurface chromophores, ultimately useful in possible photoacoustic imaging of skin and its pathology.

Consider now the apparatus and probe for burn depth profiling. The photoacoustic probe 10 used for burn depth profiling is similar to the probe 10 used for PWS profiling. It is comprised of a 1000 µm diameter optical fiber 34 for laser light delivery and a polyvinylidene fluoride (PVDF) piezoelectric detector 18 for acoustic detection similar to FIG. 1, but with a single fiber optic. The number of optic fibers used is a matter of design choice and is determined by the amount of light intensity desired in the spot. The active area of the acoustic detector 18 was 200 µm. The laser spot from fiber 34 was approximately 1.1 mm in diameter.

Figure 9:
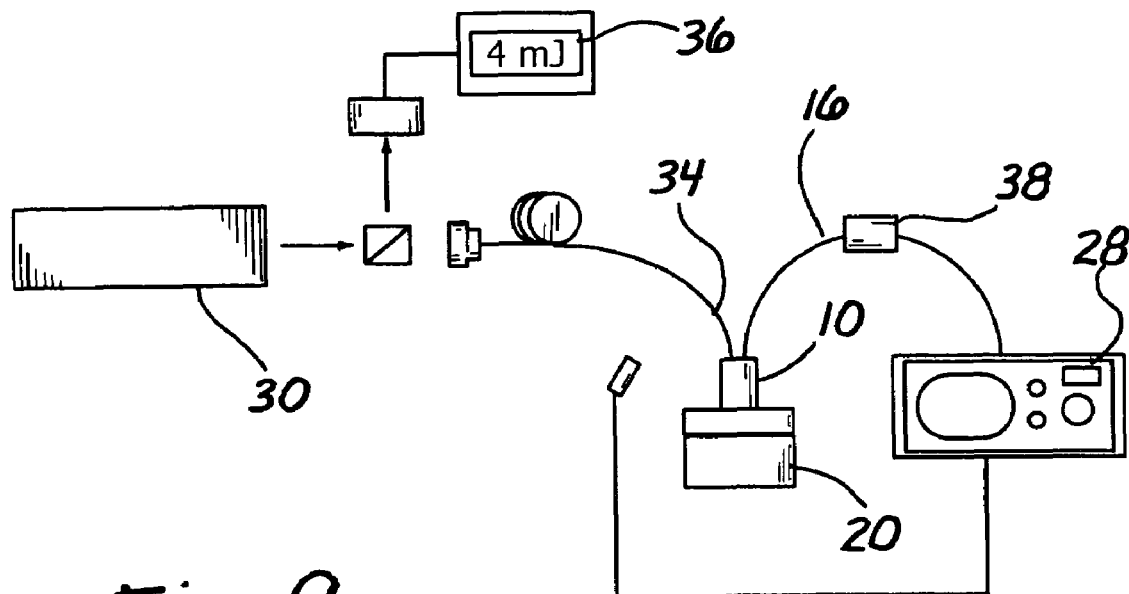
FIG. 9 is a schematic diagram of the system used for burn depth profiling in which a modified version of the handpiece of FIG. 1 is used, which modified version has a single optic fiber.

The apparatus for photoacoustic burn depth experiments is shown in FIG. 9 and comprised a frequency doubled Nd:YAG laser 30 operating at 532 nm with a pulse duration of 4 ns (Quantel Brilliant, Big Sky Laser, Bozeman, Mont.). The laser output was focused into a 1000 µm diameter quartz fiber 34 which terminated in the photoacoustic probe 10, described above. Laser energy was monitored by an energy meter 36 prior to the fiber input. Output energy from the fiber 34 was 1.5-5 mJ. Acoustic signals were detected by the piezoelectric detector 18 within the probe 10.

The voltage signal coupled to cable 16 was sent through an instrumentation amplifier 38 with a gain of 125 (SR445, Stanford Research Systems, Sunnyvale, Calif.). The amplifier had a bandwidth of 300 MHz with a 50 input impedance. The amplified signal was sent to a four channel digital oscilloscope 28 (TDS 3014, Tektronix, Wilsonville, Oreg.) with an input impedance of 1M ohm, thus the velocity potential was converted into an actual pressure signal. The oscilloscope 28 had a bandwidth of 100 MHz and sampled at 1.25 GS/s and was triggered by a photodiode which monitored laser output.

The photoacoustic waveform was analyzed and the time difference between two acoustic peaks was used to determine burn depth. For acryl amide tissue phantoms, the two peaks corresponded to two absorbing gel layers separated by a scattering layer. In the animal experiments, the two acoustic peaks corresponded to a 200 µm thick absorbing gel placed on the skin surface and the blood perfusion beneath the burned tissue.

The PS-OCT system is conventional and described in Chen, U.S. patent application Ser. No. 09/574,560, filed on May 19, 2000. The system determined microstructure and birefringence by analyzing interference fringes from the reference and sample arms of a Michelson interferometer. The system used a 1310 nm partially coherent light source (AFC Technologies, Hull, Quebec) with a bandwidth of 80 nm (FWHM). Light was coupled into an optical fiber and split equally into reference and sample arms. The reference signal was sent to a rapid scanning optical delay line.

Returning light was polarized at 45° with respect to the optical axis of the polarization modulator. The sample arm terminated in a probe with a collimator and an infinity-corrected objective lens.

The probe was mounted on a computer controlled translation stage. Return signals from the reference and sample arms were highpass filtered, digitized, and then analyzed to yield the Stokes vectors, polarization diversity intensity, and birefringence images. PS-OCT images were taken of each of the burns induced in the animals and compared with photoacoustic measurements and histological analysis.

Figure 10:
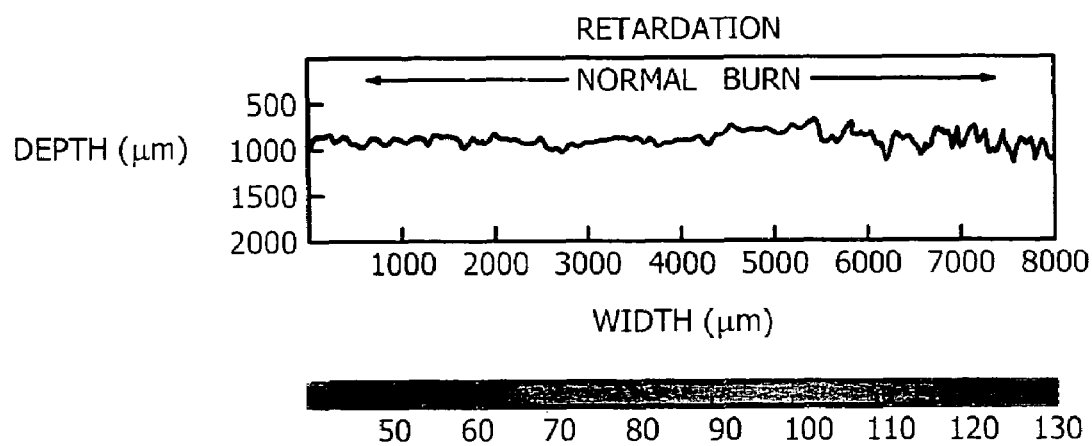
FIG. 10 is a PS-OCT phase retardation map showing the depth of a burn in rat skin.

OCT images were analyzed for burn depth in the following manner: a phase retardation map of rat skin was obtained after PS-OCT measurement as shown in FIG. 10. Skin surface is indicated by the top of the blue region along the entire width of the image. Additional phase retardation is shown in the burned region and is due to denatured collagen. Depth was determined by counting pixels in a 1000 μm wide area of the burn. The was then calculated as the average depth of each vertical column of pixels in the burned region, subtracting the corresponding depth of a 1000 μm wide section of normal tissue. 1000 μm width was chosen to approximate the laser spot size in the photoacoustic probe.

Figure 11:
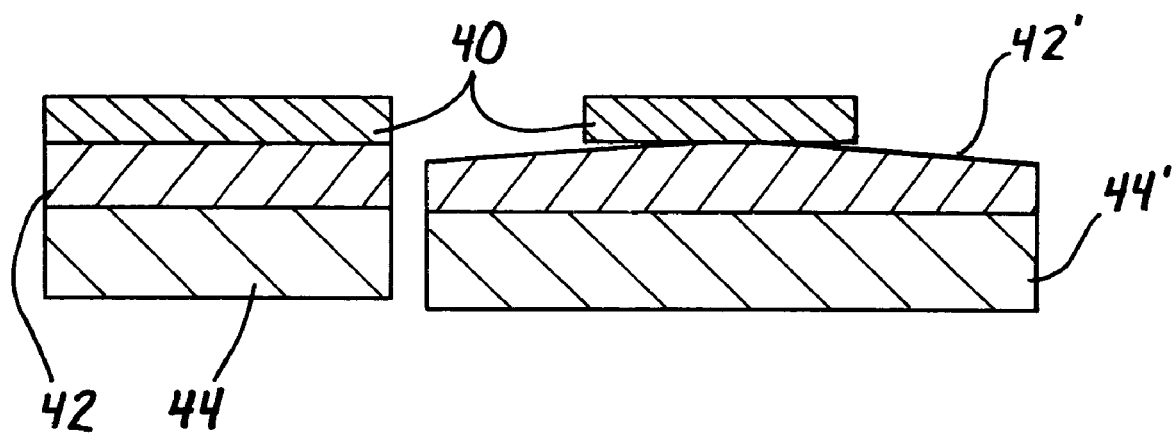
FIG. 11 is simplified side view a three-layered absorbing phantom shown on the left used to mimic the optical properties of the rat burn model shown on the right.
Figure 12A:
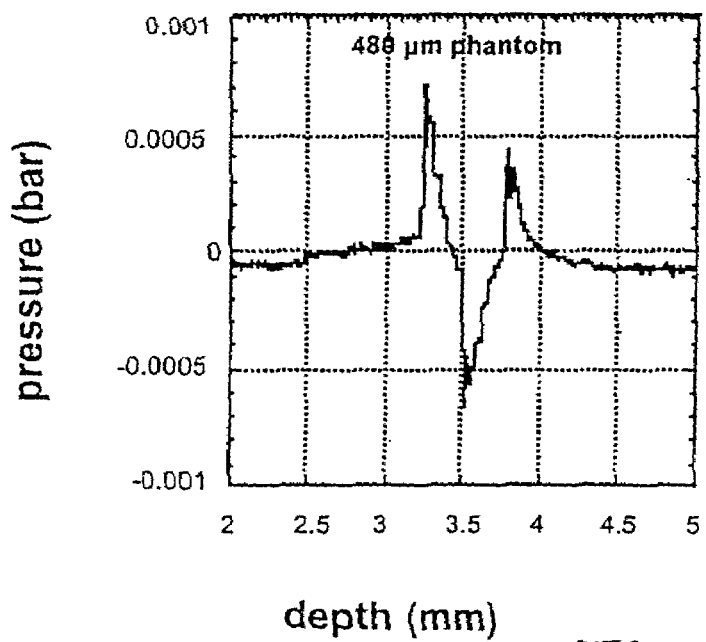
FIGS. 12a-12d are a series of graphs of the pressure verses time of the deconvoluted signal for burn phantom measurements using the phantom of FIG. 11.
Figure 12B:
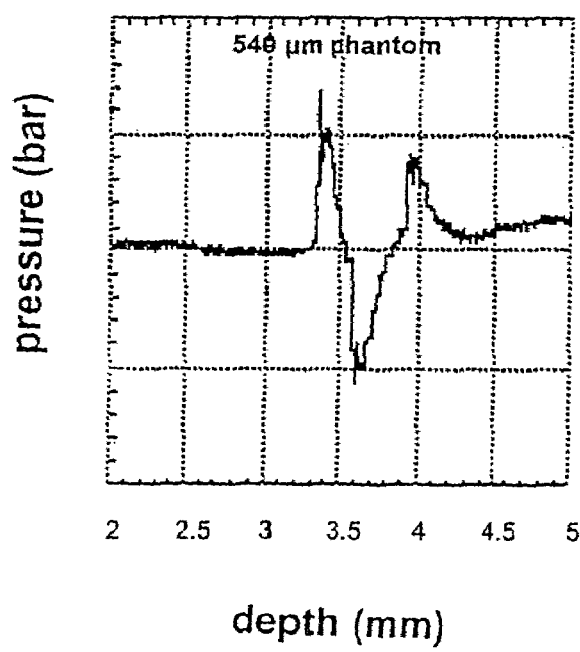
Figure 12C:
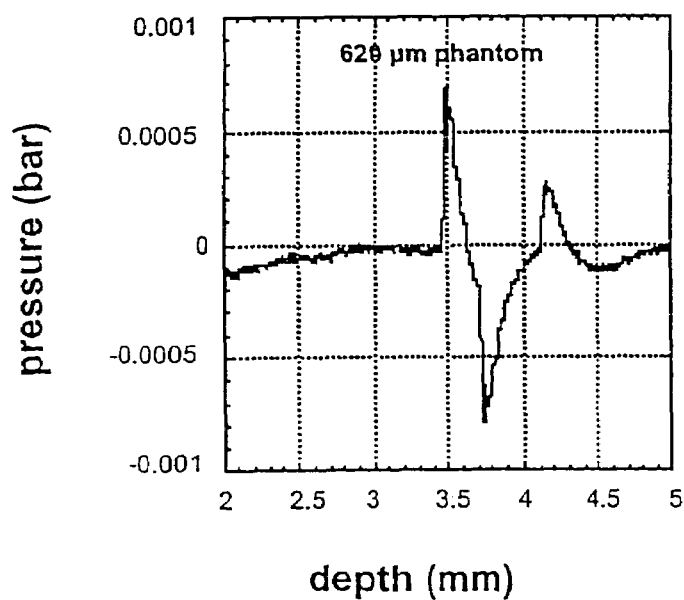
Figure 12D:
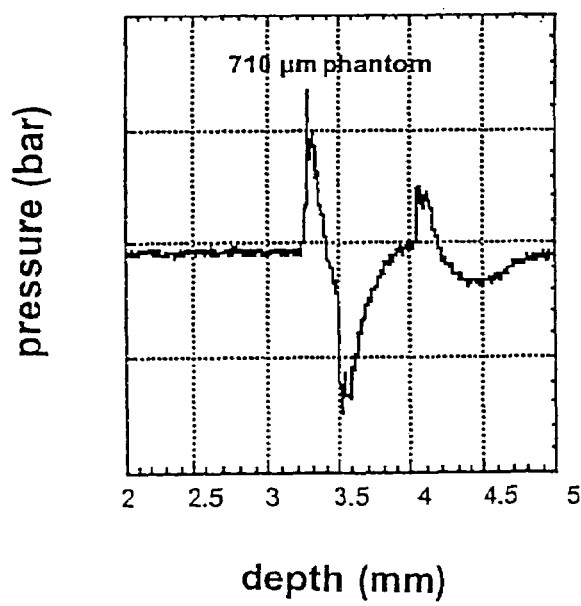
Figure 13:
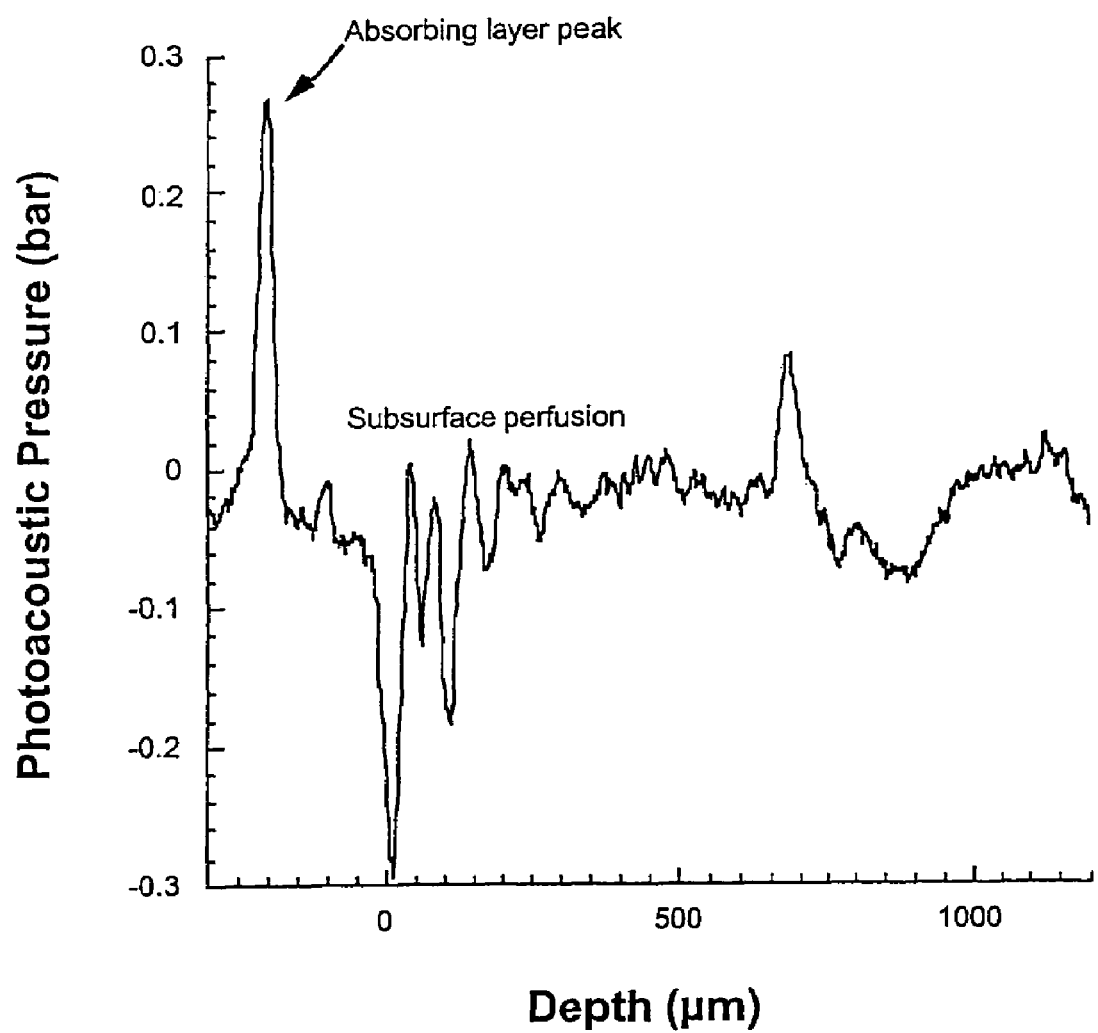
FIG. 13 is a graph of the pressure verses depth of unburned rat skin showing a strong surface peak and a weaker muscle layer at 670 μm.
Figure 14A:
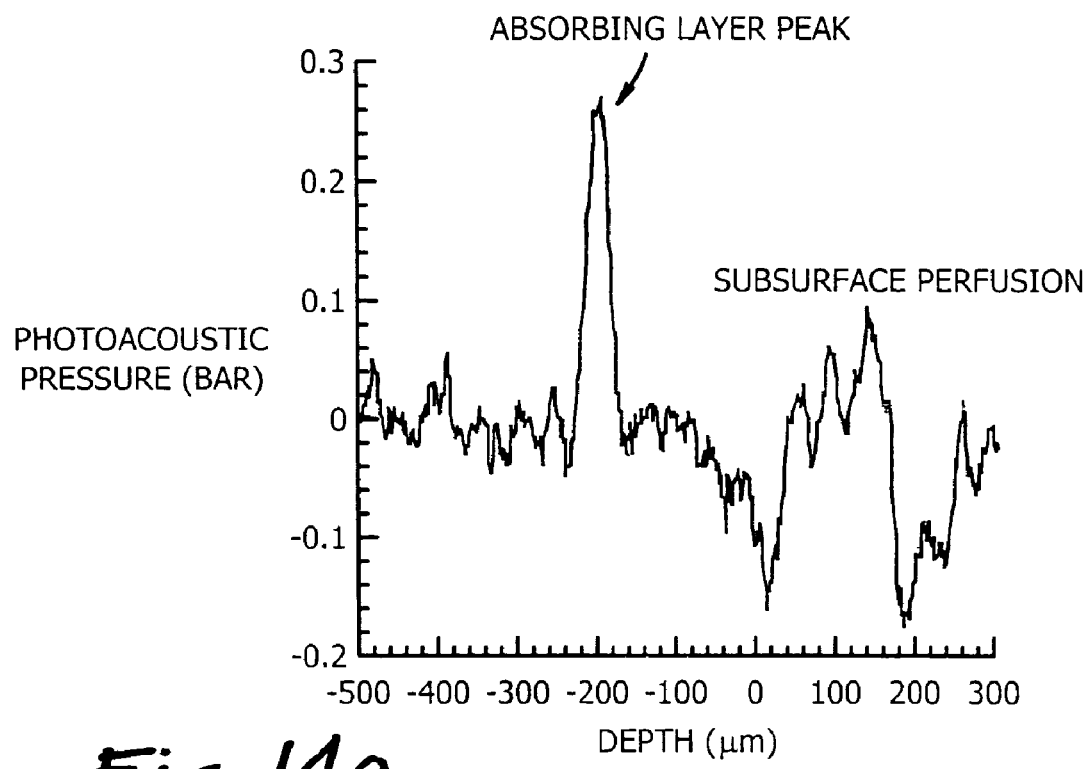
FIG. 14a is a graph of the pressure verses depth of a 5 s burn in rat skin showing signals similar to unburned skin.
Figure 14B:
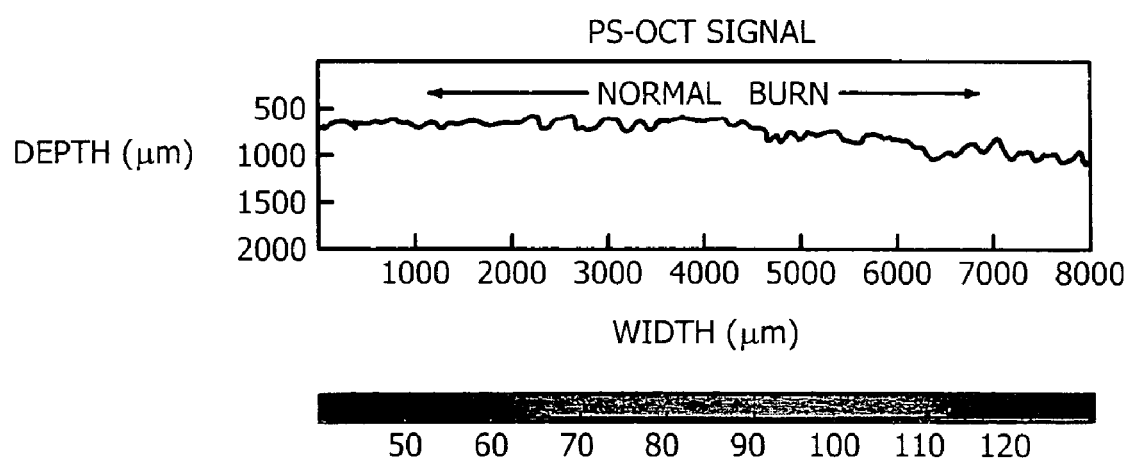
FIG. 14b is a PS-OCT map of the same burn showing little collagen denaturation.
Figure 15A:
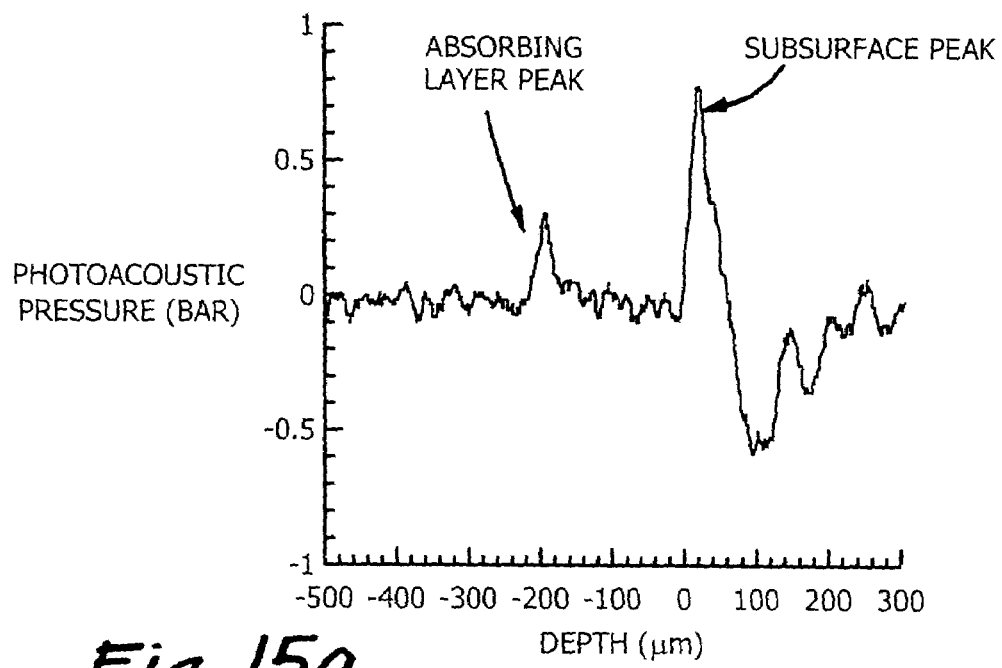
FIG. 15a is a graph of the pressure verses depth of a 10 s burn in rat skin showing a small surface peak and a strong peak at 40 μm due to edema between the epidermis and dermis.
Figure 15B:
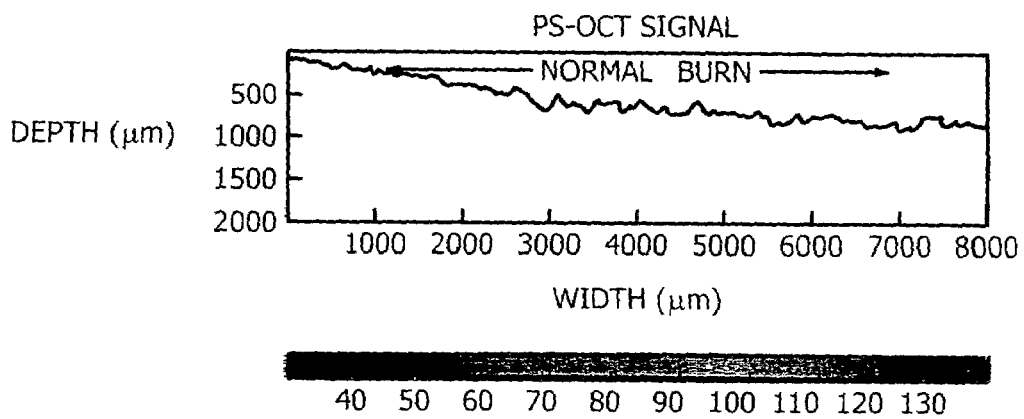
FIG. 15b is a PS-OCT map of the same burn showing little collagen denaturation.
Figure 16A:
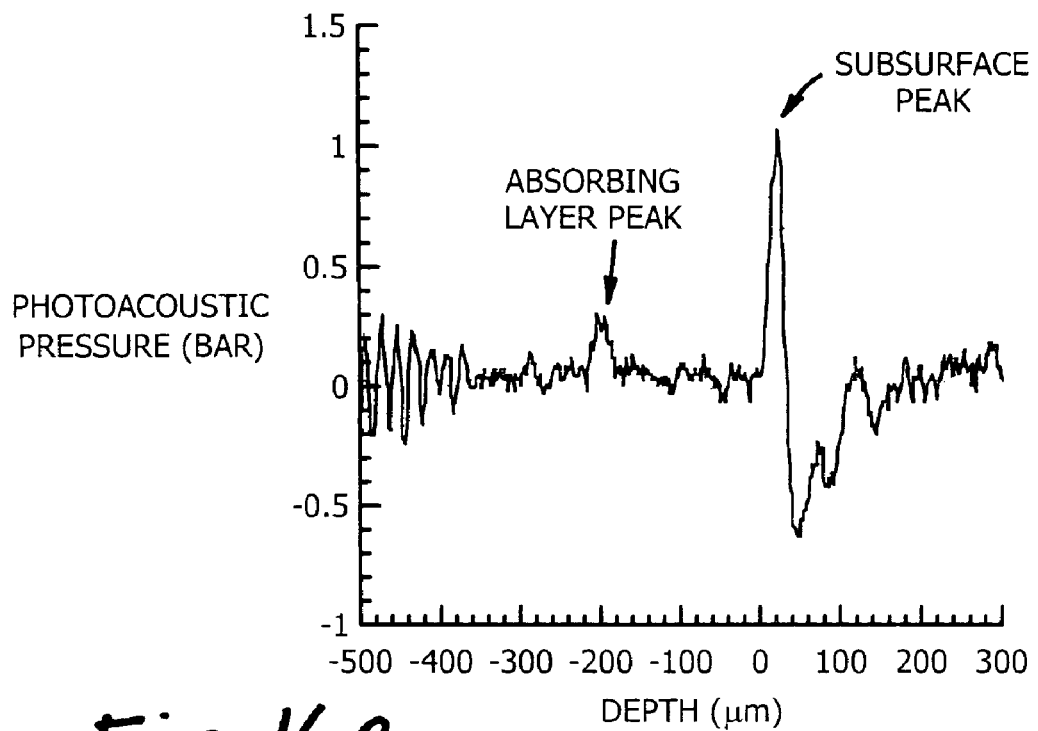
FIG. 16a is a graph of the pressure verses depth of a 20 s burn in rat skin showing a small surface peak and a strong peak at 30 μm indicating collagen denaturation.
Figure 16B:
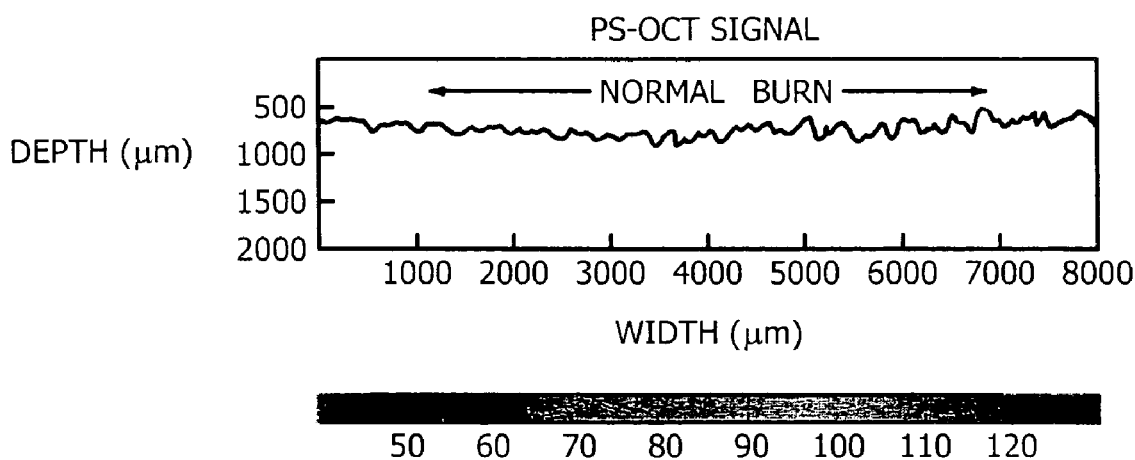
FIG. 16b is a PS-OCT map of the same burn showing some collagen denaturation up to about 50 μm.
Figure 17A:
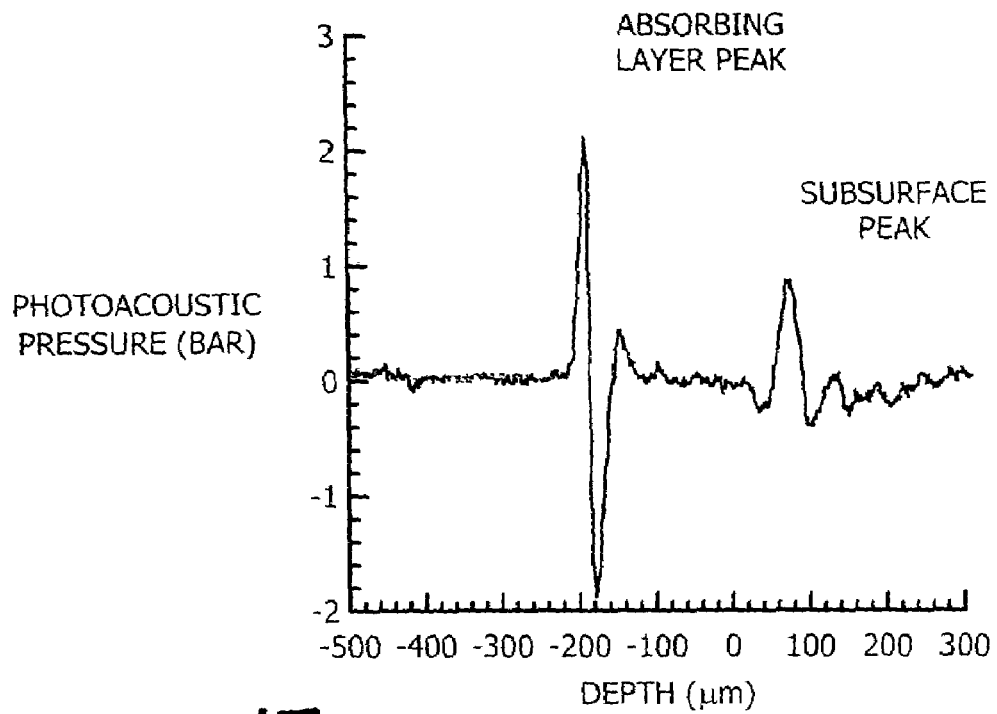
FIG. 17a is a graph of the pressure verses depth of a 30 s burn in rat skin showing collagen denaturation at 85 μm.
Figure 17B:
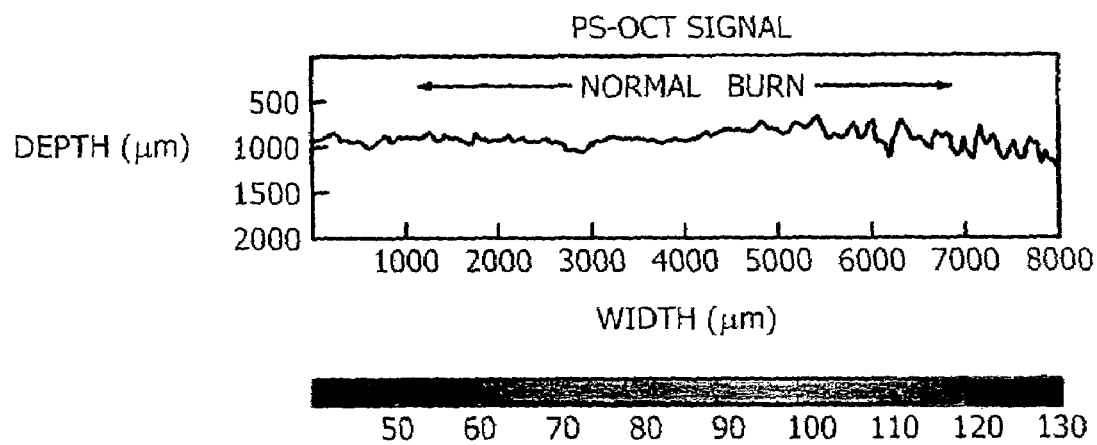
FIG. 17b is a PS-OCT map of the same burn showing 100 μm of collagen denaturation.

Acryl amide phantoms were used to simulate skin after burn injury by creating layers representing burned and viable tissue. Layer thickness and optical properties of the phantoms were chosen to mimic skin after such injury. Three layered phantoms were used in experiments as shown in FIG. 11. An absorbing acryl amide layer 40 was placed on top of a two layered phantom 42. 44 to produce a surface signal then analyzed with respect to the underlying absorbing layer, which represented the deep, viable perfused tissue 44' in burn injury. The surface was 210 μ/m thick with $\mu_a$=25 cm$^{-1}$. The actual thickness, measured with a micrometer, was slightly greater than the expected 200 μm used with the animal measurements. An intermediate turbid layer 42 represented the necrotic tissue layer 42', in which there is no longer blood flow. The intermediate turbid layers 42 were 270, 330, 410, and 500 μm thick. Intralipid (Abbott Laboratories, Abbott Park, Ill.) was added to the acryl amide solution so that $\mu_s$=200. The underlying layer 44 representing perfused tissue 44' was 1 mm thick. It was also turbid, $\mu_s$=200 cm$^{-1}$ and $\mu_a$=25 cm$^{-1}$.

Three specimens from *rattus norvegicus* of the Sprague-Dawley strain were used for burn depth experiments. Animals weighed approximately 150 g. Rats were anesthetized with ketamine hydrochloride (87 mg/kg, IP) and xylazine (13 mg/kg, IP). Animal backs were shaved and then cleaned with a surgical scrub. The end of a 1 cm diameter brass rod (weight 313 g), heated to 75° C. by a water bath, was placed on the skin to create burns on the rats.

Burn severity of the burns was determined by duration of exposure (5, 10, 20, or 30 sec.) All rats received the full range of exposures. After approximately 10 minutes, a 200 μm thick gel, used to induce a surface signal from the photoacoustic probe, was placed on the burn area and the resulting signal measured. PS-OCT were then taken on the exact sites as the photoacoustic probe. Burn biopsies were taken approximately 2 hours after injury, followed by euthanasia of the animals. Biopsies were then taken for histological examination.

Biopsies were taken from the rats on each of the burned areas and on unburned areas as controls. Biopsies were sectioned and stained with hematoxylin and eosin (H&E) and then examined microscopically. Various degrees of thermal damage were determined by the appearance of cellular structure and collagen. Separation of skin layers, including stratum corneum from the epidermis and epidermis from dermis indicated further degrees of burn injury.

A series of photoacoustic waves is shown in FIGS. 12a-12d. The duration between the two photoacoustic peaks increases with increasing burn phantom thickness. The actual and photoacoustically determined depths are shown in Table 3.

TABLE 3

Actual thicknesses of layered acrylamide phantoms v. those determined photoacoustically.

| Layer | Actual Thickness (μm) (turbid & absorbing) | Photoacoustic Thickness (μm) | % Difference |
|---|---|---|---|
| 1 | 480 | 540 | 12% |
| 2 | 540 | 588 | 9% |
| 3 | 620 | 660 | 6% |
| 4 | 710 | 780 | 10% |

Figure 18:
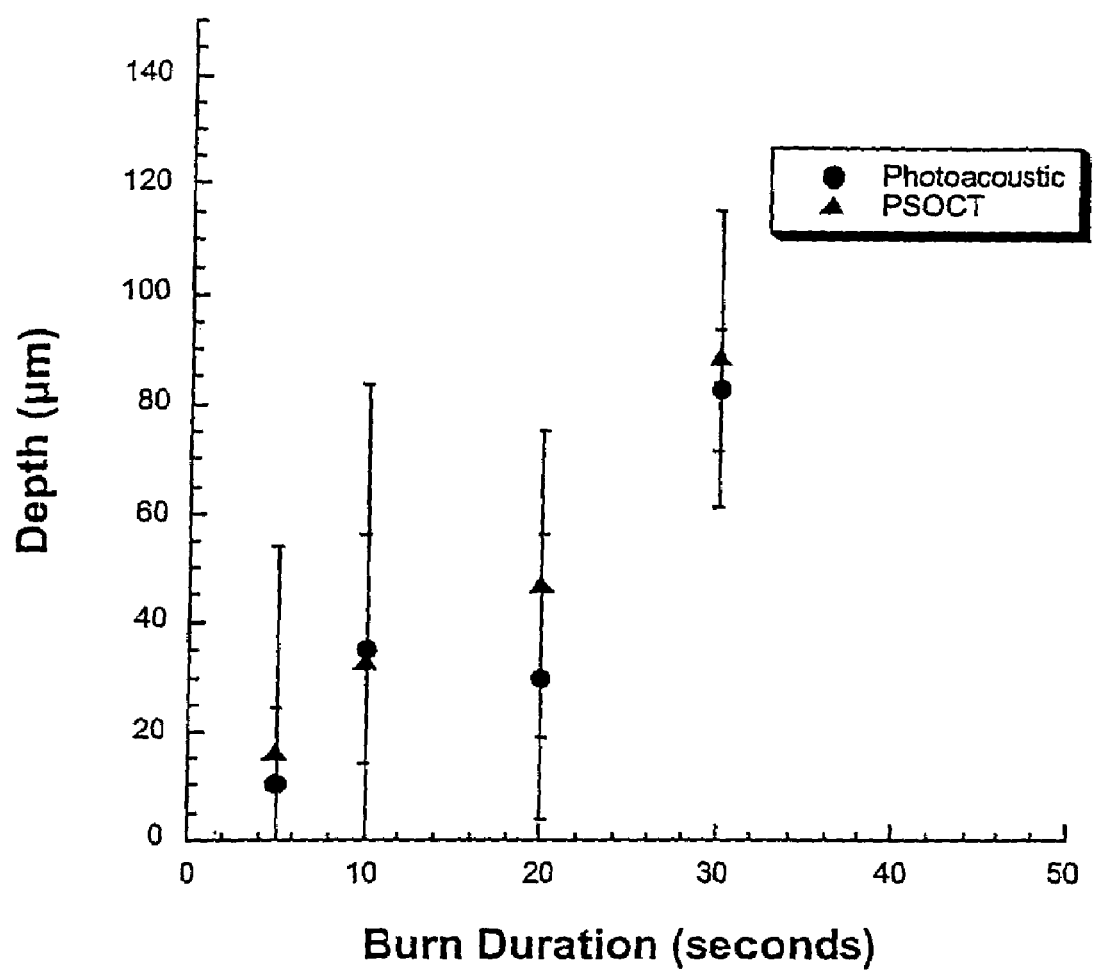
FIG. 18 is a graph comparing PS-OCT and photoacoustically determined burn depths for different burn durations.
Figure 19A:
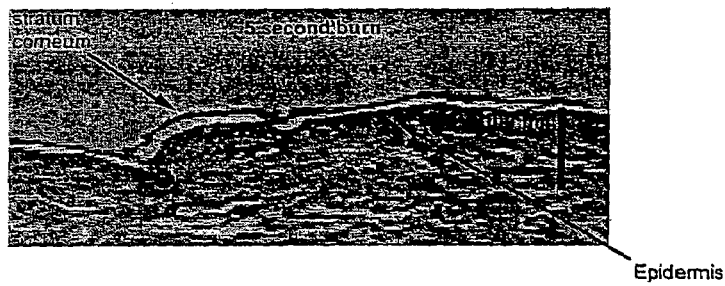
FIGS. 19a-19d are a series of microphotographs showing the evolution of burn injury in a rat model taken at 100× magnification. The 5 s burn shows little thermal damage other than vacuolization of epidermal nuclei. The 10 s burn shows greater damage to the stratum corneum and separation between the epidermis and dermis, indicating blistering. The 20 s burn shows elongated cell nuclei, indicating cell death. The stratum corneum is entirely gone and some collagen denaturation is present. The 30 s burn shows complete removal of the epidermis and deeper collagen denaturation.
Figure 19B:
Figure 19C:
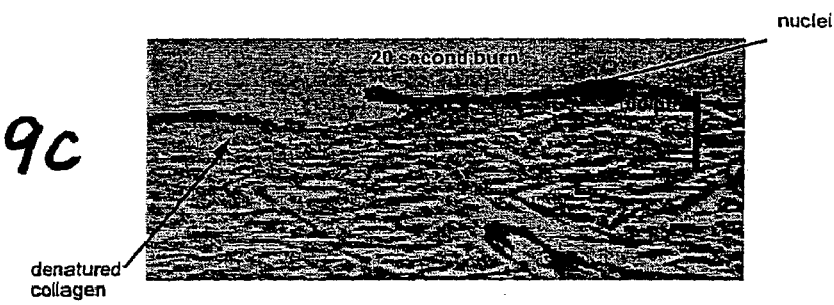
Figure 19D:
Figure 20A:
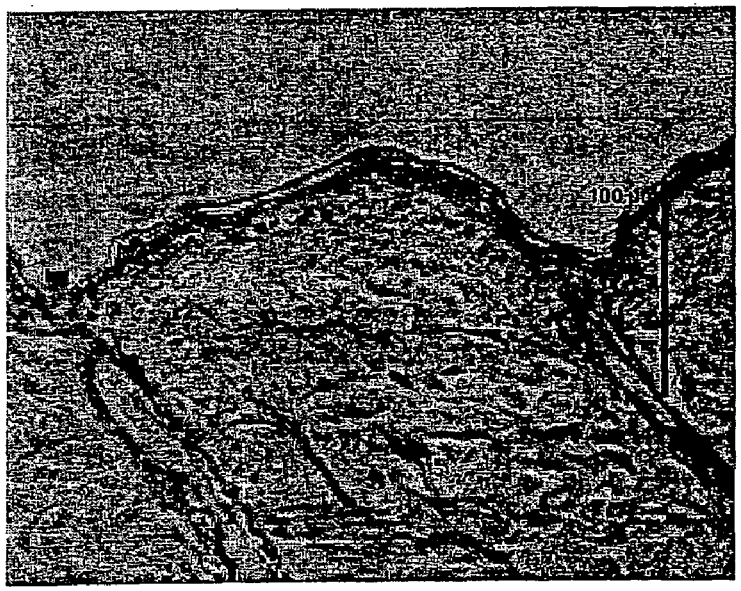
FIGS. 20a and 20b are microphotographs at 200.times.comparing burned rat skin in an upper portion and unburned rat skin in a lower portion for a 5 s burn.
Figure 20B:
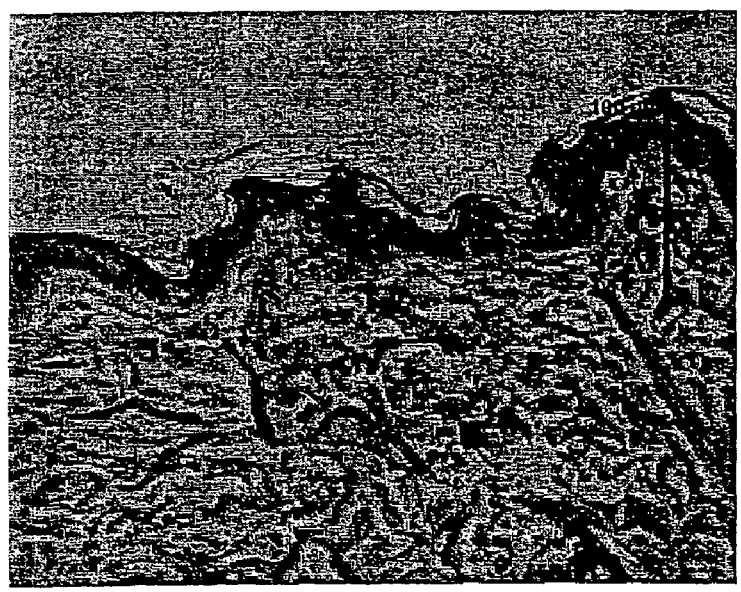
Figure 21A:
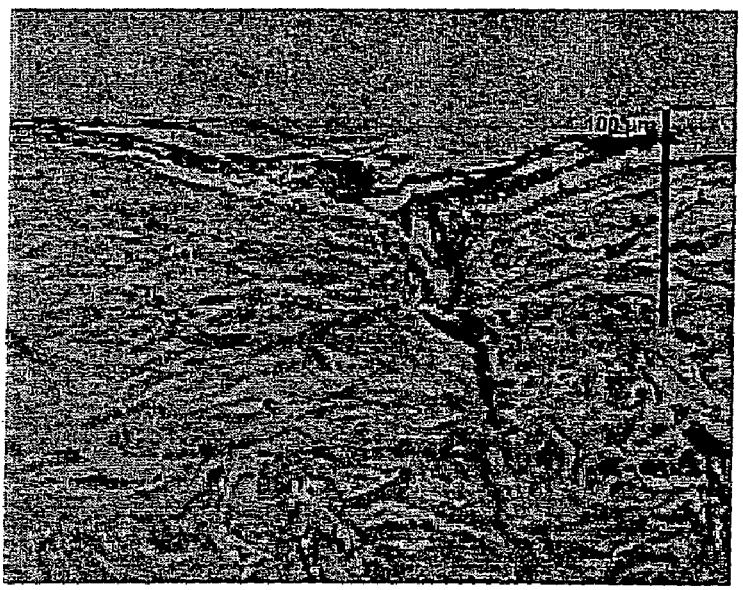
FIGS. 21a and 21b are microphotographs at 200.times.comparing burned rat skin in an upper portion and unburned rat skin in a lower portion for a 10 s burn. No collagen damage is shown.
Figure 21B:
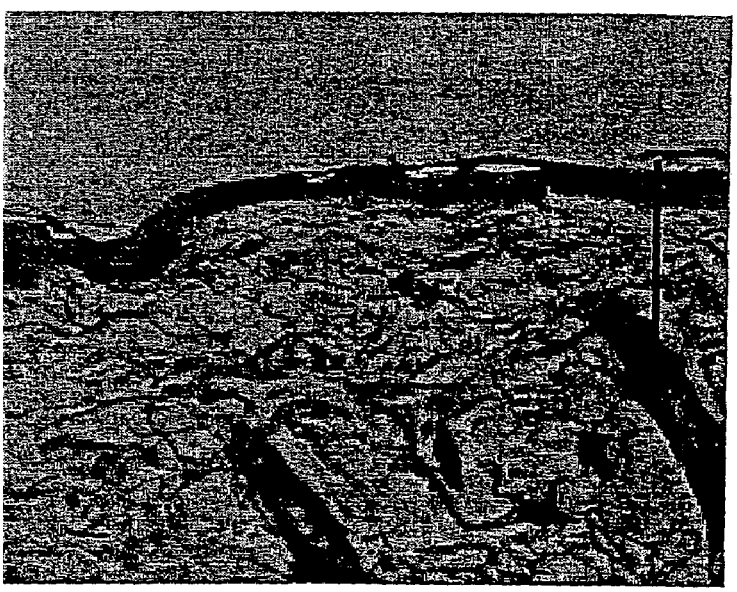
Figure 22A:
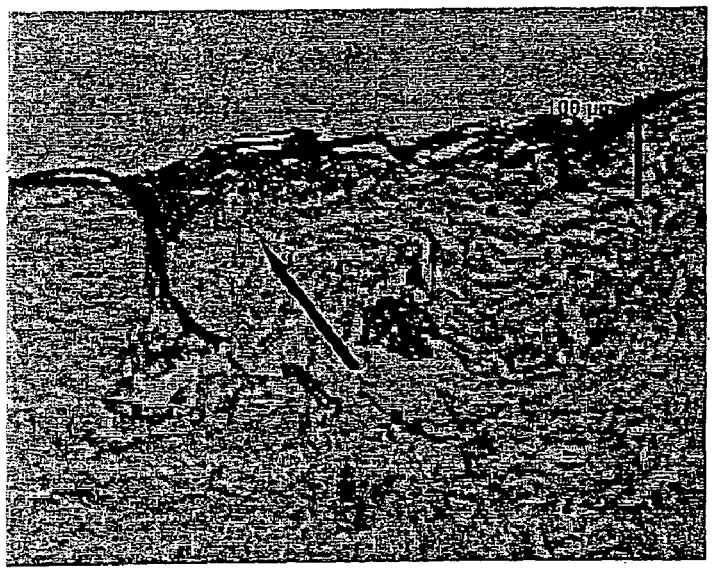
FIGS. 22a and 22b are microphotographs at 100.times.comparing burned rat skin in an upper portion and unburned rat skin in a lower portion for a 20 s burn. Some collagen denaturation is indicated by the black arrow.
Figure 22B:
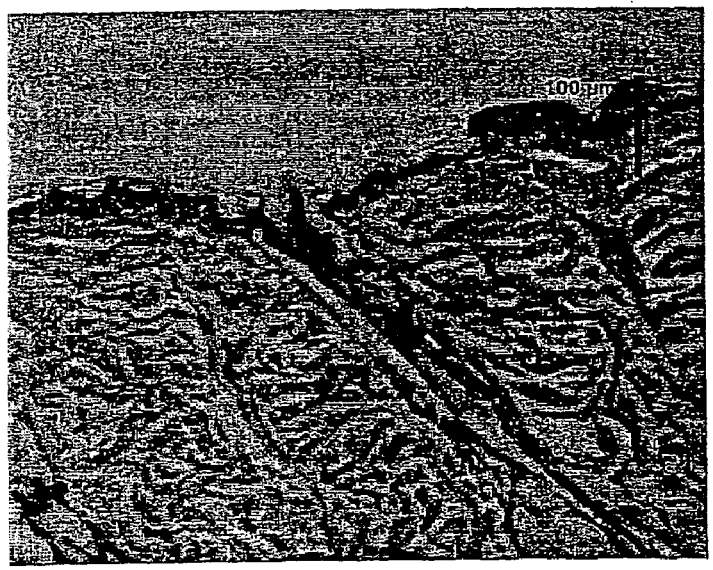
Figure 23A:
FIGS. 23a and 23b are microphotographs at 100.times.comparing burned rat skin in an upper portion and unburned rat skin in a lower portion for a 30 s burn. Burn thickness varies laterally, with approximately 70 μm of collagen damage on the left to approximately 200 μm on the right. The degree of thermal damage decreases with depth, starting with solid pink near the surface, eventually receding to normal collagen fibers below.
Figure 23B:
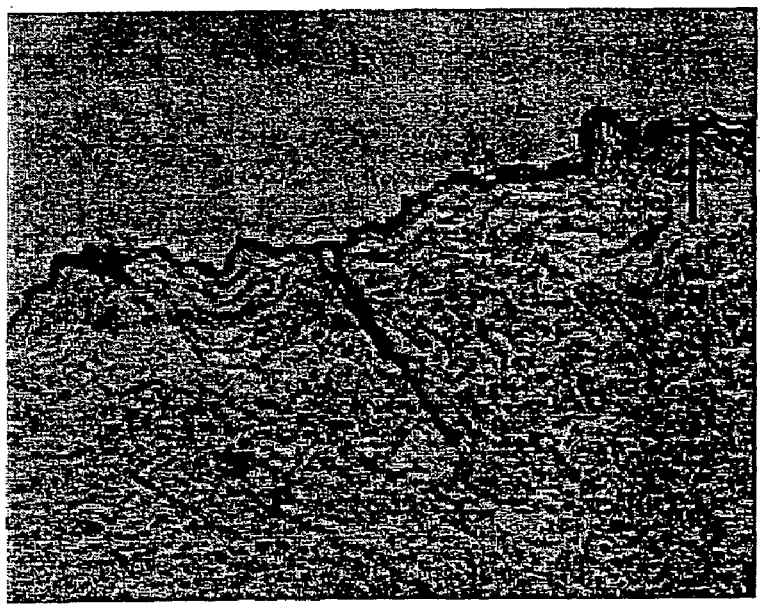

The photoacoustic signals generated in unburned, control rat skin and the 5, 10, 20, and 30 s burns are shown in FIGS. 13, 14, 15, 16, and 17, respectively. The durations between the two peaks indicated were used to determine burn depths, assuming a sound speed of 1.5 mm/μs. Depth was determined by PS-OCT using the number of pixels of low phase retardation in the burned area, indicating collagen denaturation and subtracting the number of pixels of low phase retardation in the unburned tissue. Depths of 5, 10, 20, and 30 s duration burns are shown in FIG. 18 for photoacoustic and PS-OCT measurements. Data points are averages of four measurements. A comparison of burn depths determined by photoacoustic analysis, PS-OCT, and histology is shown in Table 4.

TABLE 4

Comparison of burn depths in rats determined by photoacoustic analysis, PS-OCT, and histology

| Burn Duration (seconds) | Photoacoustic (μm) | PS-OCT (μm) | Histology (μm) |
|---|---|---|---|
| 5 | 10 | 16 | 0 |
| 10 | 37 | 33 | 0 |
| 20 | 30 | 47 | 20-80 |
| 30 | 85 | 88 | 50-200 |

A series of histological sections for the 5, 10, 20, and 30 s duration burns is shown in FIGS. 19a-19d. Mild burn injury is indicated in the 5 s sample by vacuolization of the black nuclei in the epidermis. Injury in the 10 s burn is shown by separation of the stratum corneum from the epidermis. Additionally, separation of the epidermis from the dermis is evident indicative of blister formation. In the 20 s sample, burn injury is indicated by deformed nuclei in the epidermis and total removal of the stratum corneum. If there had been blister formation, epidermal-dermal separation is no longer evident. Approximately 10-60 μm of collagen denaturation is shown by darkened pink regions near the epidermal/dermal junction. The exact depth of denaturation varies on a scale of 30-50 μm laterally. In the 30 s sample, burn injury is shown by total removal of the epidermis and by collagen denaturation near the surface, deeper than the 20 s sample, at approximately 30-120 μm.

A comparison of collagen damage between normal and burned rat skin is shown in FIGS. 20, 21, 22, and 23. No collagen damage is evident in the 5 and 10 s burns. However, in the 20 s burn, some collagen damage is shown as a more solid, darker pink area near the surface. In the 30 s burn, extensive collagen damage is evident.

By any method, burn depth determination presents many challenges which must be overcome before replacing the traditional experience of a trained burn surgeon. First, burn depth itself may be interpreted in several ways, including cellular damage, state of blood perfusion, and collagen denaturation. Additionally, the pathology of burns is dynamic, with changes taking place on the order of minutes and hours. Further changes occur over the course of the subsequent days and weeks. Any method of burn depth determination must also be easily implemented clinically, non-invasive and preferably non-contact.

The photoacoustic method described herein overcomes many of the shortcomings of previous technologies for determining burn depth, due to the unique combination of optical discrimination of tissue types and robustness of acoustic propagation. Although many techniques do not measure burn depth directly, as they are more applicable to determining whether an injury will heal without surgical intervention, the photoacoustic procedure described here attempts to give a true measure of burn depth, defined as the interface between non-perfused and perfused tissue. This boundary often corresponds to collagen denaturation in dermal burns, thus PS-OCT was used to corroborate the photoacoustic measurements.

Although the acryl amide phantoms had optical properties matched to skin, the model was much simpler than actual burn injury. The phantoms were implemented solely to test the ability of photoacoustics to determine depths between layers with thicknesses expected in burn injury. The thicknesses were accurate, with a 6-12% error, possibly due to introduction of a thin water in between acryl amide layers. The first peak, corresponding to the absorbing layer in contact with the probe, indicated the surface. The second peak indicated the subsurface absorbing layer, beneath the layer modeling the necrotic layer. The peaks from the phantoms were robust and much greater than noise and diffractive signals, indicating that the photoacoustic method, under ideal conditions, could be used for burn depth profiling.

The rat experiments showed photoacoustic signals corresponding to surface and subsurface peaks, though the delineations were much less obvious in the more superficial burns. The animal's breathing motion interfered with signal averaging, though measurements were timed with breathing to reduce such interference. The surface peaks were clearly evident in the 0 and 5 s burns, though the subsurface photoacoustic signals were weak, indicating that blood perfusion existed up to the surface, agreeing with histological analysis. The 10 s burn showed an obvious subsurface peak at about 35 µm, though this may have been due to fluid build up between the epidermis and dermis. The 20 and 30 s burns showed burn depths at about 30 and 85 µm, respectively, indicating some collagen damage down to those depths. Greater burn duration and higher temperatures should be used to test the probe further. The entire dermis of the rat is approximately 1 mm thick, which is much less than the thickest human dermis, suggesting that an alternative animal model should be used in further experiments. A porcine model with more severe burns could be used to test the probe under circumstances replicating human injury.

PS-OCT has been studied for burn depth determination. Results have shown the ability to give actual depths of thermal injury, depending on the degree of damage to dermal collagen. PS-OCT was used herein to detect the decrease in birefringence, which takes place as collagen denatures due to thermal injury (56-65° C.). Human skin can be 1-5 mm thick, making optical penetration a problem with PS-OCT, although its use in this paper is relevant as the heat damage was less than a depth of 200 µm.

All histological sections were stained with progressive H&E. Skin structures were inspected microscopically, with thermal damage indicated by changes in the shape of cellular nuclei, separation of layers such as stratum corneum, epidermis, and dermis, and collagen denaturation. The photoacoustic technique is based on the concept that capillaries in thermally damaged collagen would be destroyed, so that there would be no perfusion in the burned layer. Collagen damage was shown histologically by a melted appearance of the fibers, as opposed to the fibrous, ribbon-like appearance of normal collagen. Such damage was not evident in the 5 and 10 s burns, though some thermal damage was evident by separation of the stratum corneum and vacuolization of epidermal nuclei. The 10 s burn also showed separation between the epidermis and dermis, which may be evidence of blistering. This would have increased the burn depth measurement, as shown in the photoacoustic data. Histological inspection showed dermal collagen damage in the 20 and 30 s burns, depths corresponding to the photoacoustically determined depths. In order to fully test the probe, however, such collagen damage must be induced deeper into the skin, perhaps as much as 3-5 mm. These burns showed no blistering, perhaps due to the fusing of collagen preventing fluid buildup at the epidermal-dermal junction. Further burn depth experiments should be done with an alternative stain, such as Masson's trichrome, which permits greater discrimination between normal and thermally damaged collagen. With such staining, thermally damaged collagen appears red, while normal collagen is blue. This color discrimination would aid histological analysis of burns.

The probe 10 could also be used to monitor changes in burn depths over time, in the range of minutes to weeks. Photoacoustically determined burn depth could then be correlated with known pathological changes in burns.

Finally, a two wavelength approach to photoacoustic burn depth profiling, which exploits the difference in absorption of hemoglobin and its breakdown products in coagulated blood, could be implemented.

Under microscopic examination of burned tissue, we noted capillaries with erythrocytes in the region of denatured collagen. There would be some absorption of 532 nm light in these structures, although the absorption spectrum is different than in hemoglobin found in viable erythrocytes due to the progression of hemoglobin breakdown during heating. Using a two wavelength scheme, photoacoustic signals from healthy and thermally damaged erythrocytes could be discriminated, increasing the robustness of the photoacoustic technique. Since spectral peaks between hemoglobin and hemoglobin breakdown products will shift, laser irradiation at wavelengths corresponding to spectral peaks can be used to determine the relative concentration of hemoglobin and coagulated blood products.

Photoacoustic measurements of phantoms were accurate to within 10% of the actual thickness. A systematic error of 40-70 µm was apparent in these measurements. If this error is attributed to a thin water layer introduced during phantom preparation, the photoacoustic measurement was accurate to within 5% in 480-710 µm thick phantoms. Photoacoustic measurement of burn depth was performed in rats. The results were compared to PS-OCT measurements and histological analysis. The photoacoustic and PS-OCT results showed no collagen denaturation in 5 and 10 s burns. The 20 and 30 s burns showed approximately 30 and 85 µm of denaturation photoacoustically and 50 and 100 µm using PS-OCT. Using histology no collagen denaturation was shown in the 5 and 10 s burns, with collagen damage of about 50 and 100 µm depth for the 20 and 30 s burns, respectively.

Consider now the use of the probe 10 of the invention for use for determination of melanin depth. FIG. 9 used for burn probing shows the apparatus for photoacoustic measurements which consisted of a laser, optical fiber, photoacoustic probe, and detection electronics for melanin profiles as well. Laser energy ranged from 3-6 mJ per pulse, so that the radiant exposure was approximately 150-350 J/cm$^2$.

Figure 24:
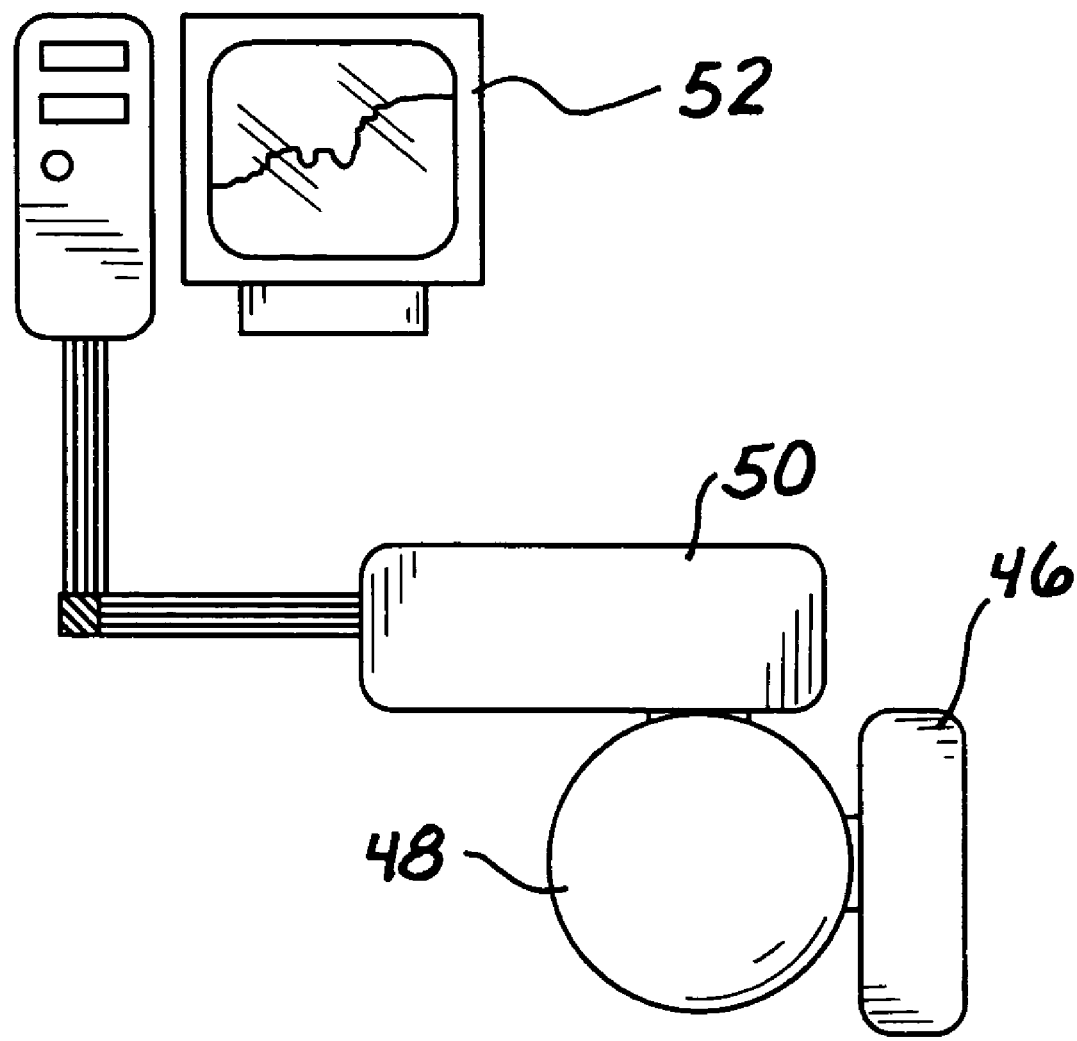
FIG. 24 is a simplified schematic showing an apparatus for making a VRS measurement of melanin concentration.
Figure 25A:
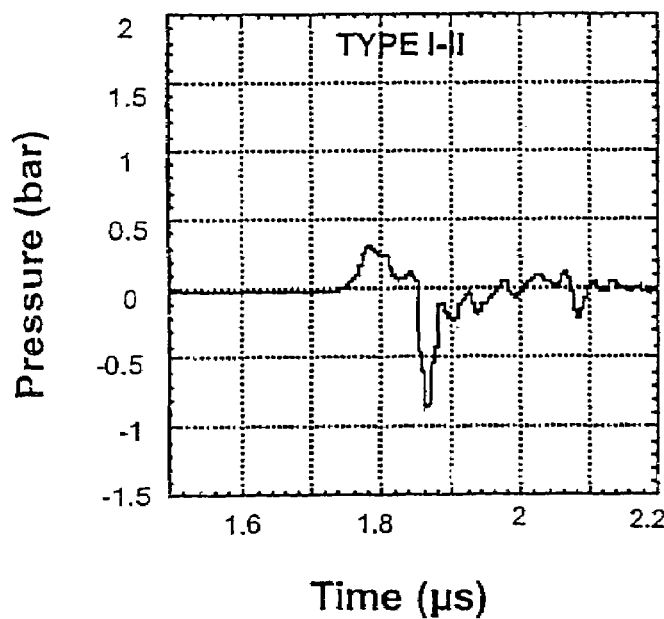
FIGS. 25a-25d are a series of graphs of the pressure verses time of the deconvoluted signal for four categories of skin phototypes. Melanin concentration is related to the area under the first peak.
Figure 25B:
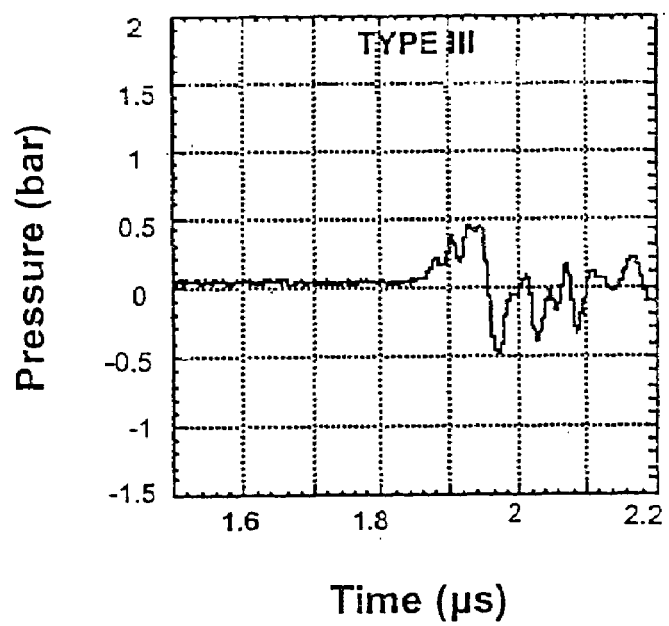
Figure 25C:
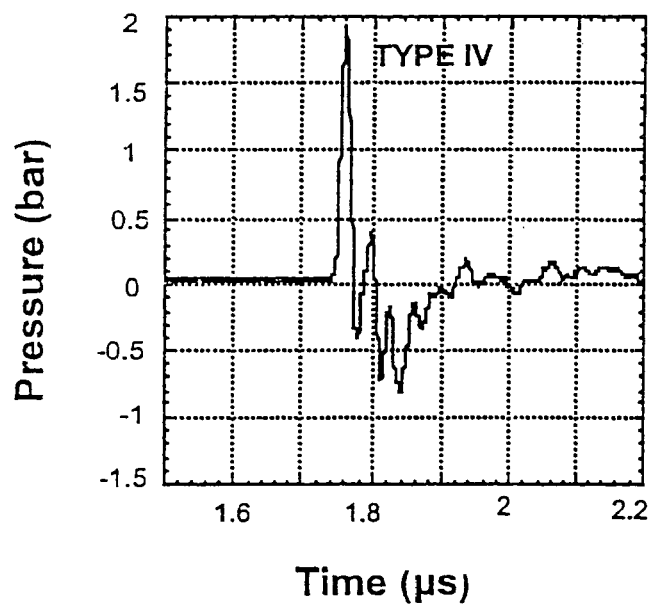
Figure 25D:
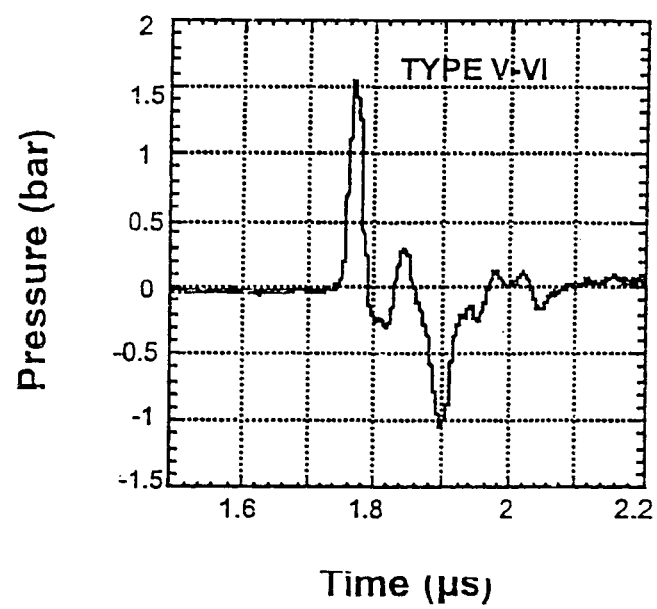
Figure 26A:
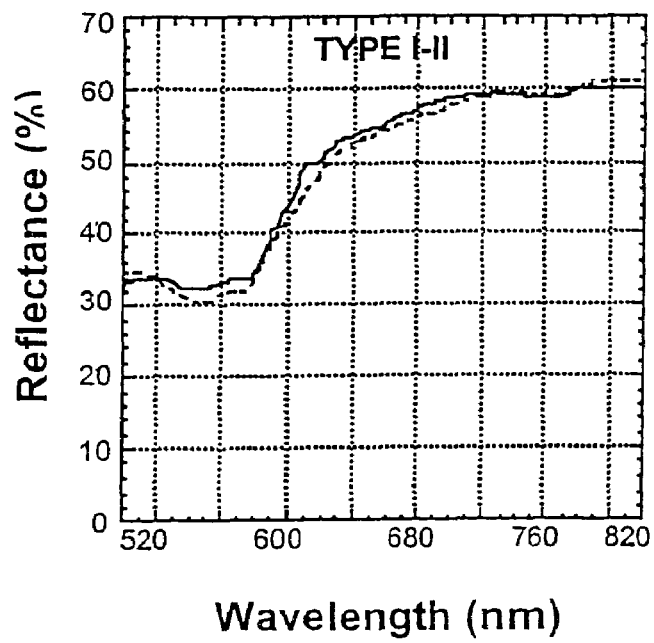
FIGS. 26a-26d are a series of graphs of reflectance verses wavelength in VRS measurements for four categories of skin phototypes. VRS measurements and diffusion model fits for the four categories of skin phototype. Spectra are shown as solid lines, while model fits are shown as dotted lines. Melanin concentration is inversely related to the slope of the spectra from 585-630 nm, where increasing slope indicates decreasing melanin concentration. The small peak at 655 nm in the type III spectrum is detector artifact.
Figure 26B:
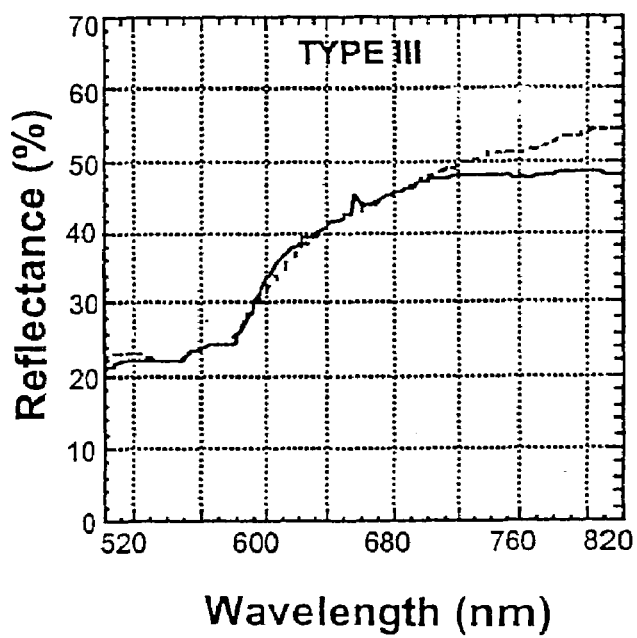
Figure 26C:
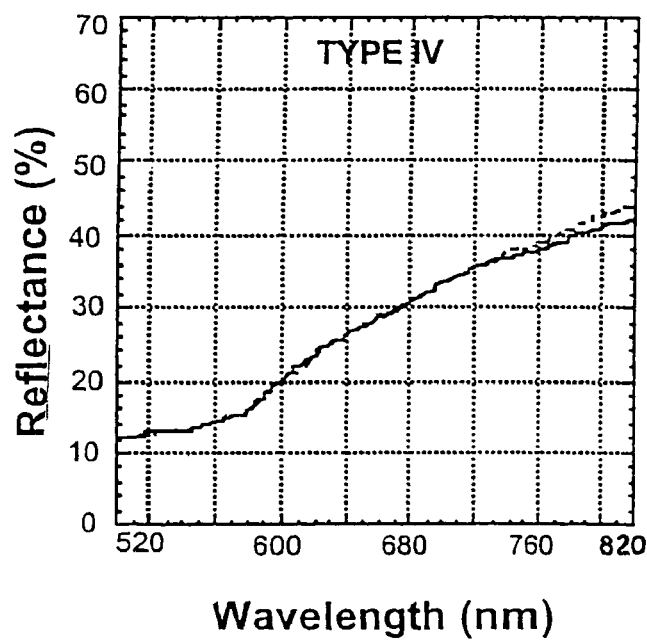
Figure 26D:
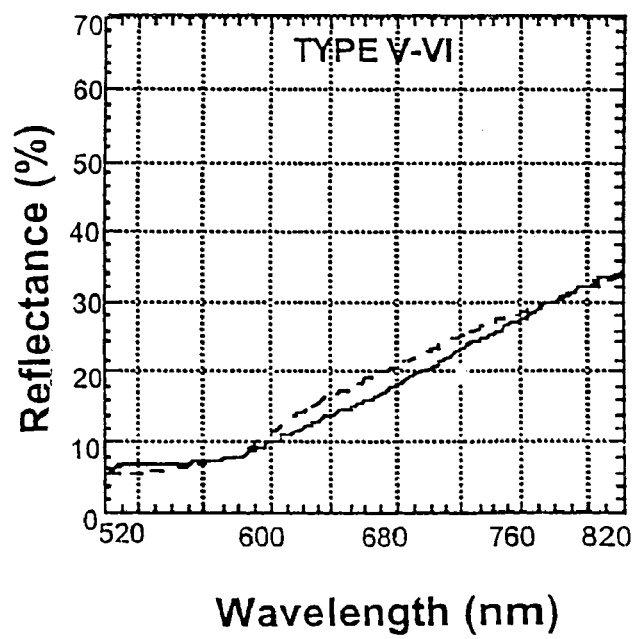

The apparatus for performing the comparative VRS measurements was comprised of a spectrometer, white light source, integrating sphere, and computer diagrammatically depicted in FIG. 24. The spectrometer 50 (HP 8452A, Hewlett Packard, Palo Alto, Calif.) was optimized for 190-820 nm, although our measurements were confined to 500-820 nm. The wavelength accuracy was 2 nm. The light source (not shown) was a tungsten halogen lamp positioned in the integrating sphere 48 (RSA-HP-84, Labsphere, North Sutton, N.H.) which was coupled to spectrometer 50. The spectrometer 50 was controlled by a Pentium computer 52 (Emachines, Irvine, Calif.). The skin surface 46 of human subjects was positioned at the 1" diameter sampling port of the integrating sphere 48 and sampled with an integration time of 500 ms. We used UV-Visible ChemStation software (Hewlett Packard, Palo Alto, Calif.) as an interface to the spectrometer 50. We used a 99% diffuse reflectance standard (WS-1, Ocean Optics, Dunedin, Fla.) to calibrate the skin measurements.

Photoacoustic waves were induced by irradiating with a stress confined laser pulse. The laser energy was delivered with a pulse duration short enough (4 ns) such that the resulting acoustic energy did not have sufficient time to propagate outside of the volume of light absorption during the pulse. Photoacoustic generation was achieved by the mechanism of thermoelastic expansion caused by rapid heating of tissue. For laser irradiation on a planar absorber (a good approximation of even lateral distribution of melanin in skin) this thermoelastic expansion results in an acoustic wave having exactly the same shape as the initial thermoelastic pressure, $$p_0(z)=\tfrac{1}{2}\mu_a \Gamma H_0 \exp(-\mu_a z)$$

where $p_0(z)$ is the initial pressure at depth z, $\mu_a$ is the absorption coefficient of the absorber, and $\Gamma$ is the unitless Grueneisen coefficient, which describes the fraction of optical energy that is translated into thermoelastic expansion. The value $\Gamma=0.12$ was used. $H_0$ is the incident laser radiant exposure. The factor of ½ is due to the planar geometry of skin, indicating half of the acoustic energy travels upward, with respect to the plane, with the other half traveling downward. The upward component is what was measured from the photoacoustic wave induced in epidermal melanin. Epidermal melanin concentration was deduced from the photoacoustic signal by analysis of total acoustic energy detected. Since laser spot size (area) was constant, epidermal scattering was assumed to be consistent between human subjects, and light propagation into tissue was only about 100 µm, total acoustic energy would be directly related to melanin concentration. Acoustic pressure is described as energy per unit volume.

Since the spot size is constant, integrating the pressure along the depth of tissue would yield energy. Thus, this integral is proportional to melanin concentration and, after normalizing by total pulse energy, can be defined as a photoacoustic melanin index (PAMI). This index is still dependent on the acoustic detector active area, so scaling by active area gives a device independent PAMI. Scaling of the active area was achieved by taking the ratio of the active area to the laser spot size, hence, PAMI is dimensionless. PAMI was recorded for all photoacoustic measurements taken.

VRS measurements resulted in spectra from 500-820 nm as percent diffuse reflectance. The spectra were fitted to a diffusion model. A two layer model was developed consisting of a thin epidermis, usually 100 µm thick, over a semi-infinite dermis. Absorption in the epidermis was primarily due to melanin and a small fraction of blood, accounting for vascular dermal papillas extending into the most superficial 100 µm of human skin. Dermal absorption was primarily due to oxygenated and deoxygenated hemoglobin. Hematocrit and relative blood oxygenation were variable, normally set at 0.41 and 70%, respectively. Both layers had wavelength dependent scattering, following $\lambda$−1 where $\lambda$ is wavelength, and a small background component of absorption. Additionally, water was included as an absorber in the infrared, with epidermal and dermal water contents set at 60% and 80%, respectively. Absorption and scattering were expressed as analytic functions incorporated into a computational model using Maple®(Waterloo Maple, Ontario, Calif.). Absorption by hair follicles was also included in the model, with parameters including hair color and density, melanin concentration, and shaft thickness.

Although all parameters mentioned above were variable, model fitting was primarily accomplished by varying melanin and blood concentrations, though relative blood oxygenation and background absorbance levels were also varied to improve the fit. Melanin concentration was optimized by matching the slope of the spectrum from 585 to 630 nm, where the effect of melanin on reflectance would be most evident.

We tested 20 healthy human subjects using the photoacoustic probe and VRS. Three areas were studied on each subject: left dorsal hand, left inner forearm, and central forehead. Care was taken to measure the exact same areas on each subject for photoacoustic and VRS methods. The numbers of subjects with respect to sun reactive skin type are as follows: Types I-II—5; Type III—7; Type IV—5; and Types V-VI—3. Additionally, a subject with vitiligo was tested. The vitiligo was on the subject's hands and appeared as irregular shaped 3-15 mm diameter spots.

Four photoacoustic signals representing skin types I-II, III, IV, and V-VI are shown in FIGS. 25a-25d. Pressure amplitude and total energy, indicated by the area under the waveform, increase with skin phototype.

Four VRS signals representing the same samples of skin types I-II, III, IV, and V-VI are shown in FIGS. 26a-26d. Increasing melanin concentration obscures the hemoglobin signature at 550 and 577 nm.

Photoacoustic and VRS measurements of a vitiligo spot are shown in FIGS. 27a and 27b. The photoacoustic amplitude is very low, with a small peak of less than 0.1 bar. The additional structure beyond 1.7 µs is due to diffraction. The VRS measurement shows a high reflectance, though there may be a small component of melanin in this measurement due to the fact that the input port of the integrating sphere was slightly larger than the vitiligo spot.

Figure 28:
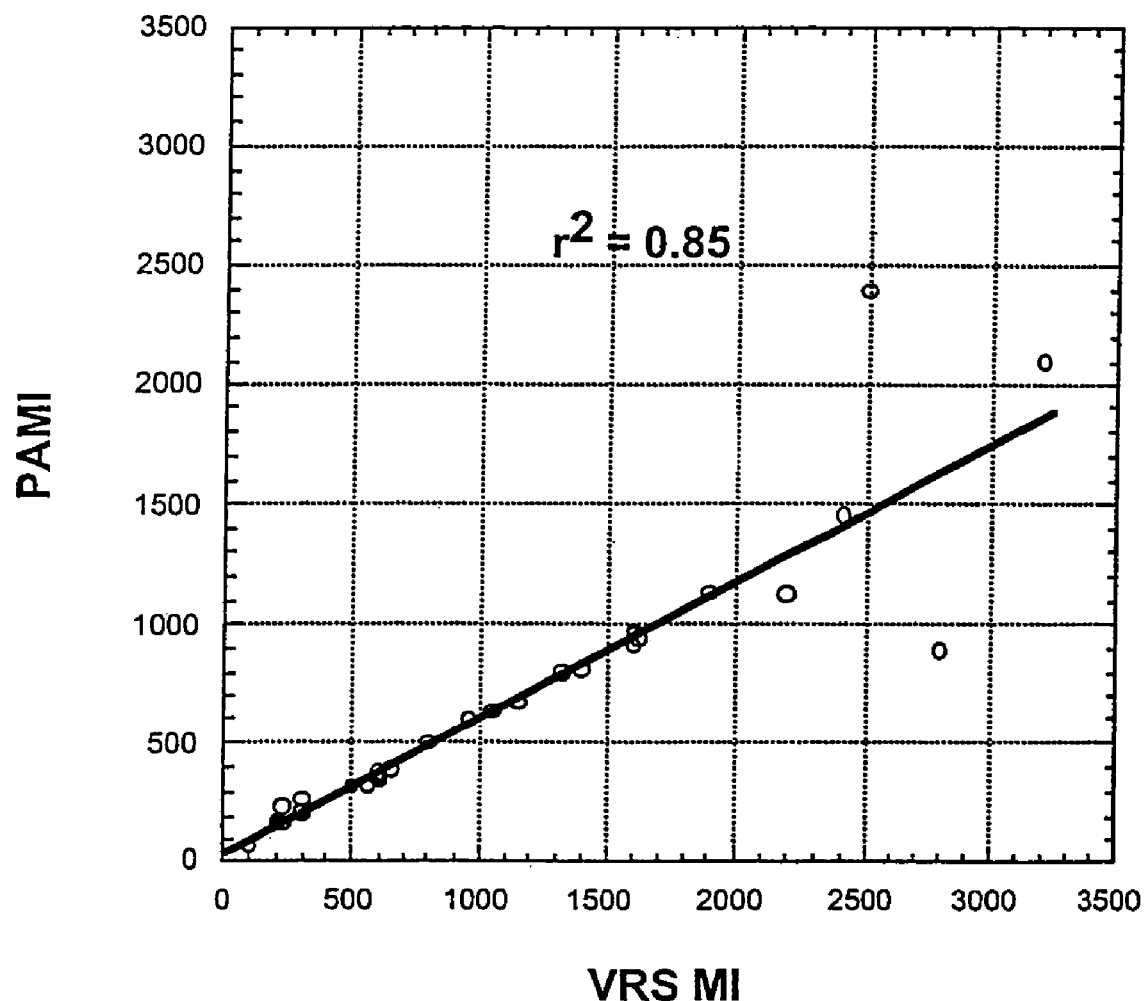
FIG. 28 is a graph of PAMI plotted against VRS measurements to show the correlation between the two measurement methods ($r^2=0.85$). The correlation breaks down for darker skin type, probably due to the small absorption depth.
Figure 29:
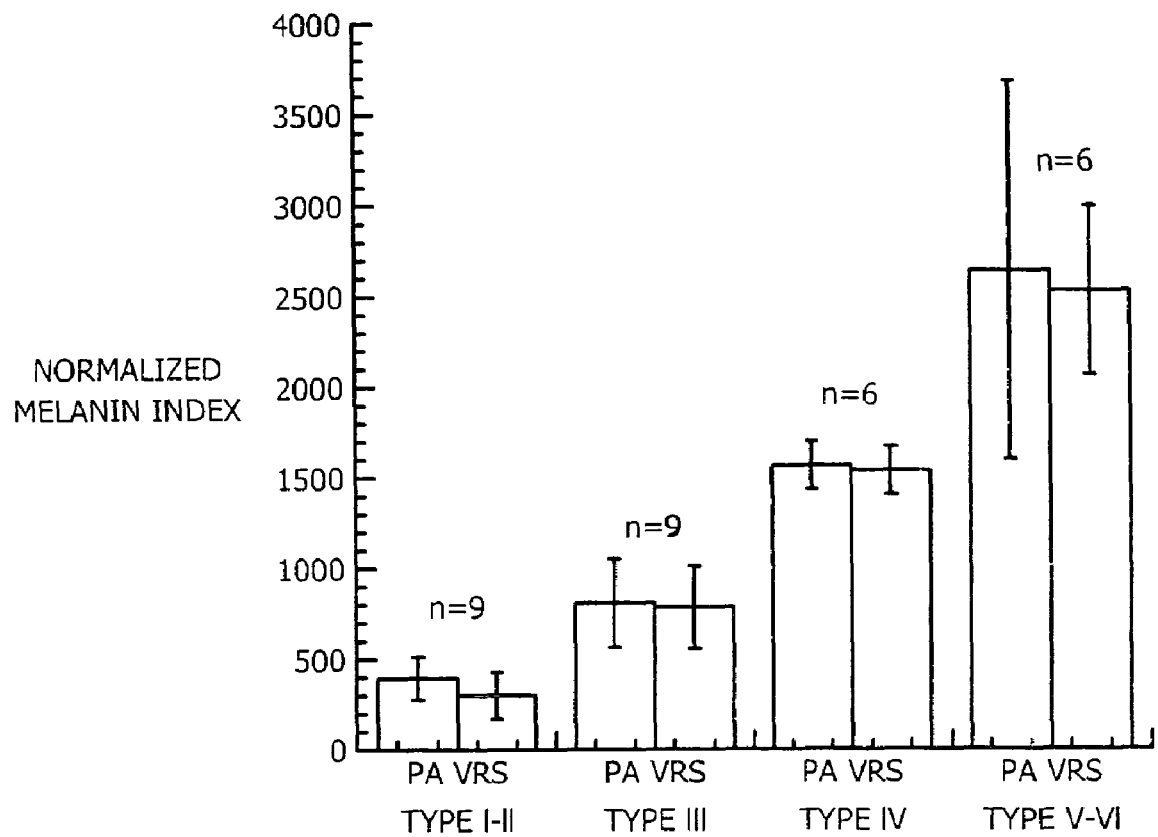
FIG. 29 is a bar graph comparing PAMI and VRS measurements of epidermal melanin for the four skin classifications, Type I-II, III, IV and V-VI.

The spectroscopic melanin index is plotted against the PAMI as shown in FIG. 28. A linear fit closely follows the data, expressed as PAMI=0.58×VRSMI+32. The correlation was good, with $r^2=0.85$. FIG. 29 shows average total melanin concentration for each skin phototype for the photoacoustic method and VRS. As expected, melanin content increases with skin phototype, though large standard deviations exist.

Accurate, repeatable measurements of epidermal melanin concentration are important for dermatologic laser procedures as well as diagnosis of pigmented dermatoses. Epidermal melanin is difficult to measure or characterize because the microscopic structure of melanosomes is not fully known. Additionally, in vitro and in vivo measurements can differ greatly from each other, as hydration, chromophore distribution, and other factors can change the mechanisms of light interaction with melanin. It has even been hypothesized that the dominant mechanism is not absorption, but scattering, based on the idea of the melanosome as a light trap in which photons are scattered therein and subsequently absorbed. Distribution of epidermal melanin is unclear. For example, some studies have shown that melanin does not extend beyond the deeper layers of the epidermis in skin phototypes I-II, while in skin phototypes V-VI it extends to the surface corneocytes. However, it has been shown that even in skin phototype II, melanin can be found in the corneocytes. Distribution of epidermal melanin is a dynamic process in which melanocytes in the basal layer transfer melanosomes to keratinocytes which subsequently degrade to melanin granules as they travel toward the skin surface.

Fortunately for the clinician performing dermatologic laser procedures, measurement of epidermal melanin concentration does not require in depth knowledge of melanosome production and transfer. The photoacoustic wave generated in skin gives the exact light distribution in the epidermis immediately after laser irradiation, thus proper light dosage can be determined from this information. If the therapeutic pulse is at a different wavelength than the diagnostic (photoacoustic) pulse, light dosage can be calculated knowing the absorption spectrum of melanin. Alternatively, the photoacoustic laser can be tuned, using an optical parametric oscillator, to match the wavelength.

VRS measurements were obtained for comparison with the results of the photoacoustic experiments. Previous studies have used Monte Carlo models and diffusion theory. We used a model based on diffusion theory, using two layers; one, with optical properties matched to the epidermis, and the second with optical properties matched to dermis. Even with the relatively simple parameters, we obtained good fits for all spectra taken. Melanin concentration was estimated by focusing on matching the slope of the spectrum from 585-630 nm, a region in which melanin absorption dominates, thus avoiding regions of high hemoglobin and water absorption. Minor departures from good fits can be seen in FIG. 26 in the skin type III measurement. The divergence between model and spectra occur after 700 nm and did not affect melanin approximation. This divergence may have been due to inexact estimation of water absorption, which is significant in this region.

Calculation of PAMI was simple and conceptually can be described as the area underneath the photoacoustic wave from the epidermal melanin and corresponds to total optical energy absorbed by melanin. As long as the epidermal thickness is less than two absorption depths, permitting 10% transmission, this approximation scheme is valid. If the epidermal thickness is much greater than two absorption depths, then the PAMI would indicate a lower bound for melanin concentration. However, such an example is likely only for very dark skin types, as the absorption coefficient for a 100 μm thick epidermis would have to be greater than 200 cm$^{-1}$, meaning that the melanin volume fraction would have to be greater than 30% throughout the entire epidermis. This analysis assumes a melanosome absorption coefficient of about 550 cm$^{-1}$ at 532 nm, which follows from, $$\mu_a = 1.70 \times 10^{12} \lambda^{-3.48}$$

which is an approximation. The duration of the photoacoustic waves gives some indication of the epidermal melanin depth profile. A longer duration implies melanin is distributed throughout the epidermis, while a short duration indicates that melanin is probably confined to the basal layer. A strict depth profile cannot be assumed from this data, however, due to the fact that the epidermal-dermal junction is non-planar.

VRS showed a low melanin concentration at the limit of the model's detection ability. The resultant photoacoustic wave showed a small peak of less than a tenth of a bar, about one order of magnitude less than the measurement for a typical Type III subject. The detection port on the integrating sphere of the VRS system was 25 mm in diameter, which was slightly larger than the actual vitiligo lesion, thus the total reflectance may have been higher.

The correlation for PAMI and VRS was good, and limiting measurements to skin types I-IV would have yielded an even better fit, as skin types V-VI showed the greater divergence. Differences in the modalities must be mentioned, however. The active area of the photoacoustic method is approximately 200 μm, making pinpoint measurements possible, though local variations, such as a nevus or hair follicle, could greatly exaggerate melanin estimation. With VRS, the melanin content is approximated from the average of a one inch diameter area, smoothing out such local variations, but making pinpoint measurements impossible. We took measures to artifacts due to abnormal pigmentation and hair follicles were avoided.

Photoacoustic measurements agreed well with the established VRS method ($r^2$=0.85), making photoacoustics an alternative for epidermal melanin measurements. Using the photoacoustic method of the invention, one may achieve depth profiling and imaging of skin structure, including epidermal melanin. While the photoacoustic waveforms shown here give some indication of the melanin depth profile, the non-planar nature of the epidermal-dermal junction requires some data analysis in order to give a proper depth profile and lateral map of epidermal structure. The addition of a scanning stage for successive measurements along with some signal processing could be employed. Using a photoacoustic depth profiling scheme or a more sophisticated inverse method could lead to epidermal imaging, providing the clinician with information not available from VRS or any other existing method.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for depth profiling subsurface skin structures comprising:
    a handpiece for* placement against the skin;
    a light source for generating a light pulse at a wavelength and intensity effective to generate an epidermal or dermal photoacoustic response;
    at least one optic fiber coupled to the light source for delivering the light pulse to the skin to generate a photoacoustic signal in the skin;
    an acoustic detector disposed in the handpiece for receiving photoacoustic waves from the skin; and
    a circuit coupled to the acoustic detector for processing electrical signals generated by the acoustic detector,
    where the acoustic detector is recessed in a probe so that it is spaced apart from the skin to provide an acoustic delay greater than the delay of electrical noise arising from the light pulse to prevent contamination of the photoacoustic signal.

2. An apparatus for depth profiling subsurface structures of burned skin comprising:
    a hand piece for placement against the skin;
    a light source for generating a light pulse at a wavelength and intensity effective to generate an epidermal or dermal photoacoustic response;
    at least one optic fiber coupled to the light source for delivering the light pulse to the skin;
    an acoustic detector disposed in the handpiece for receiving photoacoustic waves from the skin;
    circuit means coupled to the acoustic detector for processing electrical signals generated by the acoustic detector to identify acoustic signatures of dermal burn damage; and
    a plurality of optic fibers, each for delivering a light pulse to the skin, where the plurality of optic fibers each simultaneously deliver a light pulse to the skin at a single spot.

3. An apparatus for depth profiling subsurface structures of burned skin comprising:
    a hand piece for placement against the skin;
    a plurality of light sources for simultaneously generating a corresponding plurality of light pulses in a corresponding plurality of wavelengths and intensities effective to generate dermal photoacoustic responses;
    an acoustic detector disposed in the handpiece for receiving photoacoustic waves from the skin;
    circuit means coupled to the acoustic detector for processing electrical signals generated by the acoustic detector to identify acoustic signatures of dermal burn damage; and
    a plurality of optic fibers, each coupled to a corresponding one of the plurality of light sources, where each one of the plurality of optic fibers simultaneously deliver a corresponding one of the plurality of light pulses to the skin at a corresponding different wavelengths.

4. An apparatus for depth profiling subsurface structures of burned skin comprising:
    a hand piece for placement against the skin;
    a light source for generating a light pulse at a wavelength and intensity effective to generate a dermal photoacoustic response;
    at least one optic fiber coupled to the light source for delivering the light pulse to the skin;
    an acoustic detector disposed in the handpiece for receiving photoacoustic waves from the skin; and
    circuit means coupled to the acoustic detector for processing electrical signals generated by the acoustic detector to identify acoustic signatures of dermal burn damage;
    where the subsurface skin structure is a skin burn and where the electrical signals generated by the acoustic detector are interpretable as depth profiles of the skin burn.

5. An apparatus for depth profiling subsurface melanin concentrations comprising:
    a hand piece for placement against the skin;
    a light source for generating a light pulse at a wavelength and intensity effective to generate an epidermal or dermal photoacoustic response;
    at least one optic fiber coupled to the light source for delivering the light pulse to the skin;
    an acoustic detector disposed in the handpiece for receiving photoacoustic waves from the skin; and
    circuit means coupled to the acoustic detector for processing electrical signals generated by the acoustic detector to identify acoustic signatures of melanin concentrations.

6. The apparatus of claim 2 where the light source generates two selected wavelengths delivered by the plurality of optic fibers to generate corresponding different dermal photoacoustic responses from skin burn sites characterized by hemoglobin and its breakdown products in coagulated blood respectively thereby discriminating healthy from thermally damaged erythrocytes.

7. The apparatus of claim 3 where the plurality of light sources generate light at two selected wavelengths delivered by the plurality of optic fibers to generate corresponding different dermal photoacoustic responses from skin burn sites characterized by hemoglobin and its breakdown products in coagulated blood respectively thereby discriminating healthy from thermally damaged erythrocytes.

8. The apparatus of claim 4 where the light source generates light at two selected wavelengths delivered by the optic fiber to generate corresponding different dermal photoacoustic responses from skin burn sites characterized by hemoglobin and its breakdown products in coagulated blood respectively thereby discriminating healthy from thermally damaged erythrocytes.

* * * * *